US011229349B2

(12) United States Patent
Obikane

(10) Patent No.: US 11,229,349 B2
(45) Date of Patent: Jan. 25, 2022

(54) VARIABLE-MAGNIFICATION OPTICAL SYSTEM AND IMAGING APPARATUS

(71) Applicant: Tamron Co., Ltd., Saitama (JP)

(72) Inventor: Yasuhiko Obikane, Saitama (JP)

(73) Assignee: Tamron Co., Ltd., Saitama (JP)

( * ) Notice: Subject to any disclaimer, the term of this patent is extended or adjusted under 35 U.S.C. 154(b) by 223 days.

(21) Appl. No.: 16/495,182

(22) PCT Filed: Oct. 11, 2017

(86) PCT No.: PCT/JP2017/036785
§ 371 (c)(1),
(2) Date: Sep. 18, 2019

(87) PCT Pub. No.: WO2018/185955
PCT Pub. Date: Oct. 11, 2018

(65) Prior Publication Data
US 2021/0113063 A1 Apr. 22, 2021

(30) Foreign Application Priority Data
Apr. 4, 2017 (JP) .............................. JP2017-074316

(51) Int. Cl.
| | |
|---|---|
| *A61B 1/00* | (2006.01) |
| *G02B 15/14* | (2006.01) |
| *G02B 15/16* | (2006.01) |
| *G02B 23/24* | (2006.01) |
| *G02B 27/64* | (2006.01) |
| *G03B 5/00* | (2021.01) |

(52) U.S. Cl.
CPC .... *A61B 1/0019* (2013.01); *G02B 15/144105* (2019.08); *G02B 15/145113* (2019.08); *G02B 15/16* (2013.01); *G02B 23/243* (2013.01); *G02B 27/646* (2013.01); *G03B 5/00* (2013.01); *G03B 2205/0015* (2013.01)

(58) Field of Classification Search
CPC .......... A61B 1/0019; G02B 15/144105; G02B 15/145113; G02B 15/16; G02B 23/243; G02B 27/646; G03B 5/00; G03B 2205/0015
See application file for complete search history.

(56) References Cited

U.S. PATENT DOCUMENTS

| | | | |
|---|---|---|---|
| 5,748,385 A | 5/1998 | Miyano | |
| 6,035,145 A * | 3/2000 | Kanai | ............ G02B 15/144105 396/379 |
| 2004/0246592 A1 | 12/2004 | Suzuki | |

(Continued)

FOREIGN PATENT DOCUMENTS

| | | |
|---|---|---|
| JP | 854561 A | 2/1996 |
| JP | 11125770 A | 5/1999 |

(Continued)

*Primary Examiner* — Cara E Rakowski
(74) *Attorney, Agent, or Firm* — The Webb Law Firm

(57) ABSTRACT

A variable magnification optical system capable of realizing a high-resolution observation image display system that can arbitrarily change an observation field of view without changing a working distance of an observation optical system while keeping the observation optical system small in size and an imaging apparatus including the variable magnification optical system.

12 Claims, 15 Drawing Sheets

(56) References Cited

U.S. PATENT DOCUMENTS

| | | | |
|---|---|---|---|
| 2011/0085247 A1* | 4/2011 | Matsumura | G02B 15/145113 359/683 |
| 2011/0199689 A1* | 8/2011 | Ishibashi | G02B 15/144105 359/684 |
| 2011/0228407 A1* | 9/2011 | Yamaguchi | G02B 15/173 359/687 |
| 2014/0029111 A1* | 1/2014 | Shibata | G02B 15/144109 359/686 |
| 2015/0022907 A1 | 1/2015 | Yamamoto | |
| 2016/0282592 A1 | 9/2016 | Abe et al. | |
| 2017/0363846 A1 | 12/2017 | Takada | |

FOREIGN PATENT DOCUMENTS

| | | |
|---|---|---|
| JP | 2002207167 A | 7/2002 |
| JP | 2004361778 A | 12/2004 |
| JP | 201522161 A | 2/2015 |
| WO | 02057830 A1 | 7/2002 |
| WO | 2015087619 A1 | 6/2015 |
| WO | 2016129055 A1 | 8/2016 |

* cited by examiner

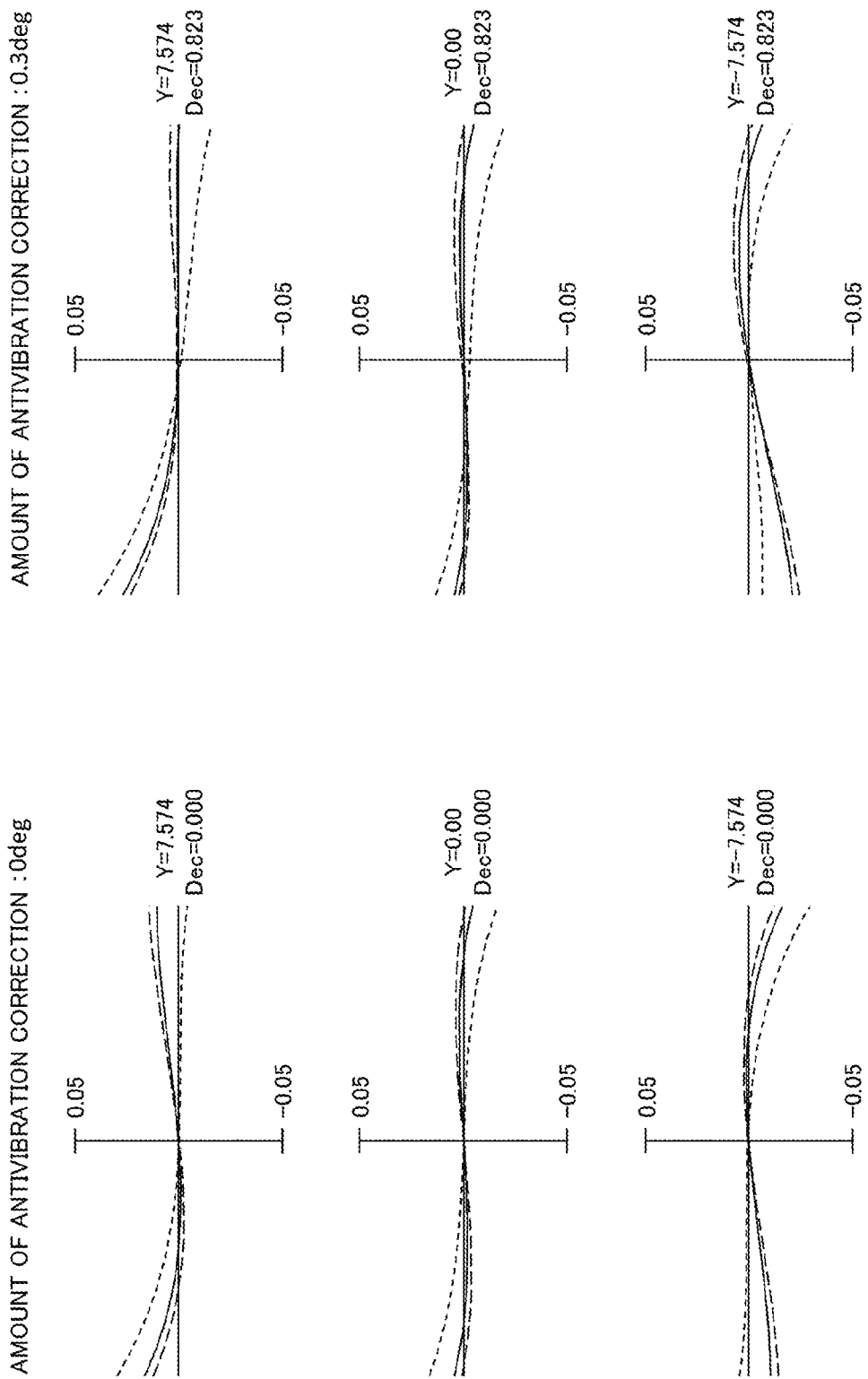

VARIABLE-MAGNIFICATION OPTICAL SYSTEM AND IMAGING APPARATUS

CROSS-REFERENCE TO RELATED APPLICATIONS

This application is the United States national phase of International Application No. PCT/JP2017/036785 filed Oct. 11, 2017, and claims priority to Japanese Patent Application No. 2017-074316 filed Apr. 4, 2017, the disclosures of which are hereby incorporated by reference in their entirety.

Technical Field

The present invention relates to a variable magnification optical system and an imaging apparatus, and particularly to a variable magnification optical system connected to an observation optical system and an imaging apparatus.

Technical Description

Conventionally, a rigid endoscope that enables internal observation of a narrow portion has been used in a medical field or an industrial field, for example. The rigid endoscope generally includes a thin cylindrical insertion section to be inserted into a narrow portion such as the inside of a body and an ocular section connected to the insertion section, an objective lens system or the like being housed in the insertion section, and an ocular lens system being housed in the ocular section. In the rigid endoscope, an object image can be directly observed via the ocular section. In recent years, a rigid endoscope image display system in which an imaging apparatus including an imaging optical system and an image sensor is connected to the ocular section to enable the object image acquired by the rigid endoscope to be displayed on a display device such as a monitor has been increasingly used.

In the medical field, endoscopic surgery using the rigid endoscope image display system has been performed. In the endoscopic surgery, a doctor or a technician performs a required treatment according to a state of an affected site while observing an object image displayed on a display device. For the endoscopic surgery, it will be enough when only some small holes are made for inserting an insertion section of a rigid endoscope and surgical instruments, such as forceps and electrocautery scalpels, into the body of a patient. Thus, the body of the patient is less stressed and post-operative recovery is also faster than in conventional open-abdominal surgery or open-chest surgery, for example. Thus, a hospital stay can be shortened. Accordingly, a public burden of medical costs can also be reduced. Further, in the future, progress is also expected in a telesurgical system for a doctor at a remote location to issue an instruction about a required treatment to another doctor who actually performs a procedure and remotely operate a surgical robot, for example, based on a state of an affected site displayed on a display device, for example. Particularly, in an underpopulated area that is short of doctors, for example, there is a need for spread of such a telesurgical system. Thus, not only for reduction of physical and economic burdens on the patient but also from a social viewpoint, there is a need for further spread or development of endoscopic surgery.

The endoscopic surgery requires a rigid endoscope image display system that enables highly precise observation of the affected site and is capable of changing an observation magnification depending on complete observation of the affected site or partial observation of the affected site, for example, in keeping with the progress of surgery. There is a similar demand for the rigid endoscope image display system used in the industrial field.

Against such a background, Japanese Patent Laid-Open No. 2015-22161 proposes an objective lens (objective lens system) for an endoscope that performs focusing by moving at least one or more lens group(s) excluding a lens group closest to an object side along an optical axis. In the objective lens for an endoscope described in Japanese Patent Laid-Open No. 2015-22161, a working distance (a distance between a distal end of the objective lens for an endoscope and an affected site (an object)) is changed to enable enlarged observation of the affected site by reducing the working distance. However, in the objective lens for an endoscope described in Japanese Patent Laid-Open No. 2015-22161, a focusing mechanism such as a cam for moving a movable lens group needs to be provided within an insertion section. Accordingly, the insertion section is difficult to miniaturize. To perform the enlarged observation of the affected site, the distal end of the objective lens for an endoscope needs to be brought closer to the affected site. However, the distal end of the objective lens for an endoscope may be unable to be brought closer to the affected site for a reason such as avoiding interference with surgical instruments, and the enlarged observation of the affected site may be unable to be sufficiently performed.

Japanese Patent Laid-Open No. 8-54561 proposes an objective lens for a variable field angle endoscope that includes a front group lens having positive refractive power and a rear group lens having negative refractive power, where the rear group lens is moved between two positions, i.e., a first rear group lens position and a second rear group lens position so as to change a working distance or an image viewing angle. In the objective lens for a variable field angle endoscope described in Japanese Patent Laid-Open No. 8-54561, the rear group lens is in focus when moved between the above-described prescribed two positions. Thus, a focusing mechanism need not be provided in an insertion section in a rigid endoscope. Accordingly, the diameter of the insertion section can be easily reduced. However, if either one of the working distance and the image viewing angle of the objective lens for a variable field angle endoscope described in Japanese Patent Laid-Open No. 8-54561 is changed, an image viewing angle or an observation distance corresponding thereto is determined. That is, an observation magnification cannot arbitrarily be changed without the observation distance being changed. Accordingly, enlarged observation of an affected site may be unable to be sufficiently performed for a reason such as avoiding interference with surgical instruments, for example, like in Japanese Patent Laid-Open No. 2015-22161.

Japanese Patent Laid-Open No. 11-125770 proposes an imaging optical system used while being connected to an ocular section in a rigid endoscope. The imaging optical system described in Japanese Patent Laid-Open No. 11-125770 includes a first lens group to a fourth lens group in this order from an ocular section side, and performs focusing by respectively moving the second lens group having negative refractive power and the third lens group having positive refractive power at the time of zooming and moving the entire first lens group or its part in an optical axis direction at the time of focusing. When the imaging optical system is connected to the ocular section in the rigid endoscope, focusing and zooming can be performed without providing a zooming mechanism or a focusing mechanism within an insertion section in the rigid endoscope. Accordingly, if the imaging optical system disclosed in Japanese Patent Laid-Open No. 11-125770 is used, enlarged observation of an affected site, for example, can arbitrarily be performed while miniaturizing the insertion section and maintaining a working distance in which interference with surgical instruments can be avoided. However, in the imaging optical system disclosed in Japanese Patent Laid-Open No. 11-125770, the first lens group arranged closest to an observation optical system side is moved in the optical axis direction to perform focusing. Thus, an optical overall length fluctuates at the time of focusing. The imaging optical system is arranged within a lens barrel, and is constructed as a lens unit. When the optical overall length of the imaging optical system fluctuates, a lens barrel length of a lens barrel portion that houses the imaging optical system is also required to be made variable. At the time of surgery, disinfection, bacteria elimination, sterilization, and the like are also required for the lens unit. However, if the lens barrel length is variable, a lens barrel structure becomes complicated. Thus, it is difficult for the lens unit to have a watertight structure or a waterproof structure capable of disinfection, bacteria elimination, sterilization, and the like of the lens unit.

[Patent Literature 1] Japanese Patent Laid-Open No. 2015-22161

[Patent Literature 2] Japanese Patent Laid-Open No. 8-54561

[Patent Literature 3] Japanese Patent Laid-Open No. 11-125770

SUMMARY

Given the foregoing, an object of the present invention is to provide a variable magnification optical system, capable of realizing a high-resolution observation image display system that can arbitrarily change an observation field of view without changing a working distance of an observation optical system while keeping the observation optical system small in size, and an imaging apparatus including the variable magnification optical system.

The inventors of the present invention have solved the above-described problem by adopting a variable magnification optical system, described below, as a result of a diligent study.

A variable magnification optical system according to the present invention is a variable magnification optical system connected to an observation optical system and including a first lens group arranged closest to an observation optical system side, a final lens group arranged closest to an image side, and a plurality of movable lens groups arranged between the first lens group and the final lens group and movable in an optical axis direction, wherein the first lens group and the final lens group are fixed in the optical axis direction, and the plurality of movable lens groups are moved in the optical axis direction, to perform zooming, and at least one of the plurality of movable lens groups is moved in the optical axis direction to perform focusing on a nearest point object from a farthest point object.

An imaging apparatus according to the present invention includes the variable magnification optical system described above, and an image sensor that converts into an electrical signal an optical image formed by the variable magnification optical system on the image side of the variable magnification optical system.

According to the present invention, there can be provided a variable magnification optical system capable of realizing a high-resolution observation image display system that can arbitrarily change an observation field of view without changing a working distance of an observation optical system while keeping the observation optical system small in size and an imaging apparatus including the variable magnification optical system.

DRAWINGS

FIG. 25 is a lateral aberration diagram in the telephoto end state of the variable magnification optical system in Example 5 of the present invention; and FIG. 26 is a schematic view illustrating an example of an imaging apparatus according to the present invention.

DETAILED DESCRIPTION

Figure 1:
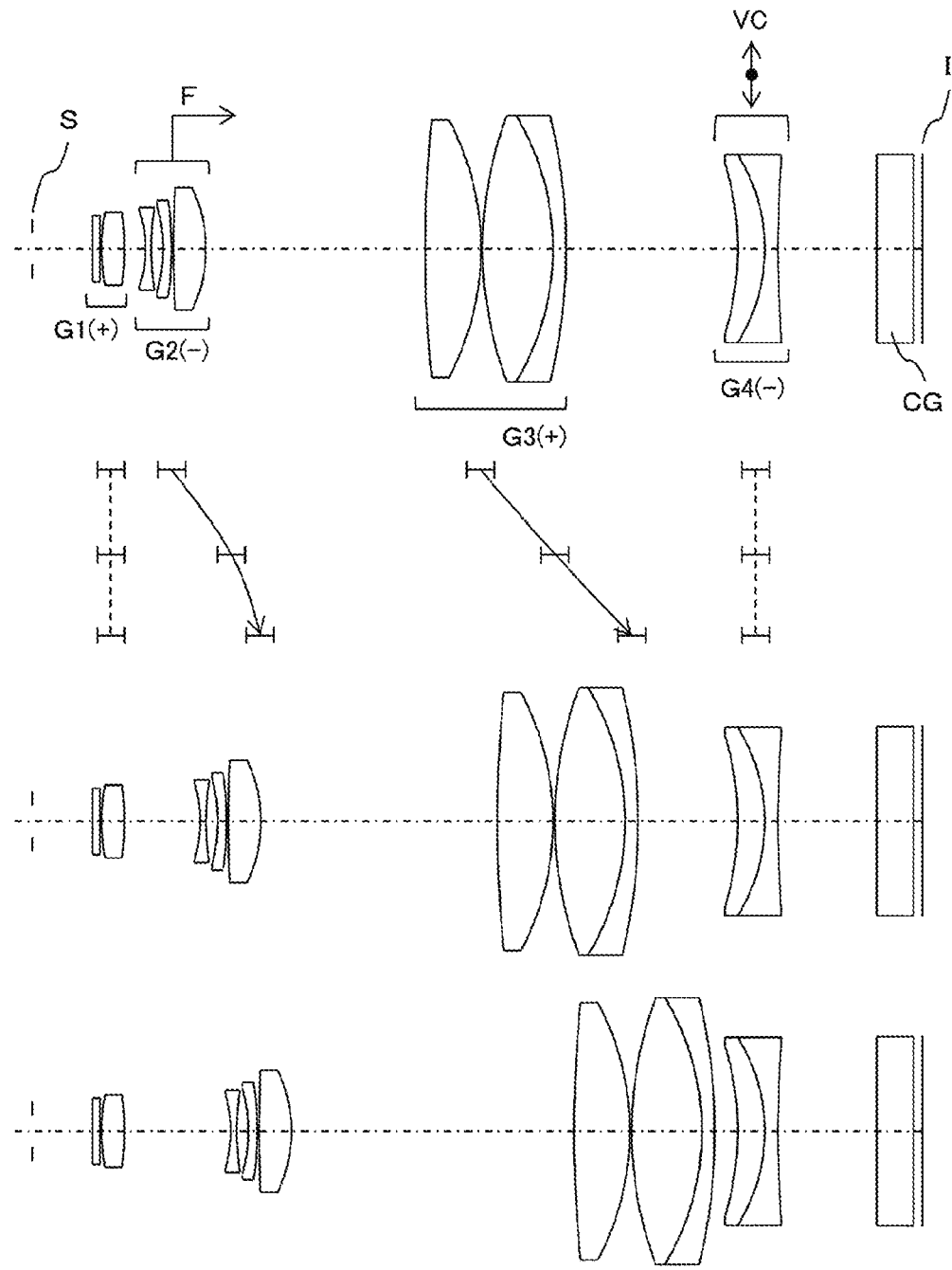
FIG. 1 is a diagram illustrating a lens construction example of a variable magnification optical system in Example 1 of the present invention, where the upper part is a lens construction diagram at a wide angle end, and the lower part is a lens construction diagram at a telephoto end.

Embodiments of a variable magnification optical system and an imaging apparatus according to the present invention will be described below.

1. Variable Magnification Optical System

A variable magnification optical system according to the present invention is a variable magnification optical system connected to an observation optical system, which is characterized by including a first lens group arranged closest to an observation optical system side, a final lens group arranged closest to an image side, and a plurality of movable lens groups arranged between the first lens group and the final lens group and movable in an optical axis direction, in which the first lens group and the final lens group are fixed in the optical axis direction, and the plurality of movable lens groups are moved in the optical axis direction, to perform zooming, and at least one of the plurality of movable lens groups is moved in the optical axis direction to perform focusing on a nearest point object from a farthest point object.

1-1. Observation Optical System

First, the observation optical system will be described. The observation optical system is generally an optical system including an objective lens system and an ocular lens system and constructed to form a primary object image (real image) by the objective lens system and bring the primary object image into substantially parallel light by the ocular lens system. Note that, some observation optical systems may be each constructed to form a plurality of intermediate object images by arranging a relay lens system between the objective lens system and the ocular lens system and extending the total length of the lens by the relay lens system.

The variable magnification optical system according to the present invention is connected to an ocular section in the observation optical system, for example. Note that, the ocular section in the observation optical system mainly refers to a lens barrel section that houses the ocular lens system, and generally refers to a component or a region referred to as an ocular lens or eyepiece, for example. An observer can observe an object image via the ocular section.

Specific examples of the observation optical system can include a microscope and a rigid endoscope. The variable magnification optical system is used while being connected to the ocular section in the observation optical system. Particularly, a case where the variable magnification optical system is used while being connected to the ocular section in the rigid endoscope will be described below as an example.

The rigid endoscope generally includes an insertion section having a thin cylindrical shape to be inserted into a narrow portion and an ocular section connected to the insertion section, and the objective lens system is housed in the insertion section and the ocular lens system is housed, as described above, in the ocular section. In a rigid endoscope used in a medical field, an insertion section is inserted into the body of a patient via a hole or the like made on the body, and an ocular section is arranged outside the body. To secure a length of the insertion section, the above-described relay lens system, together with the objective lens system, may be housed in the insertion section, or a relay section that houses the relay lens system may be connected between the insertion section and the ocular section. It is possible to realize a rigid endoscope image display system for displaying an object image acquired by the rigid endoscope on a display device such as a monitor, by connecting an imaging apparatus including the variable magnification optical system, the image sensor, and the like to the ocular section in the rigid endoscope can be realized.

Note that, the variable magnification optical system according to the present invention is not limited to the mode connected to the ocular section in the rigid endoscope but can be connected to ocular sections in various observation optical systems such as a microscope. By connecting the variable magnification optical system to the ocular sections in the observation optical systems, it is possible to realize a similar observation image display system to that described above. Further, the variable magnification optical system can be used as an image forming optical system such as an imaging optical system by the variable magnification optical system alone without being connected to the ocular section in the observation optical system.

1-2. Construction of Variable Magnification Optical System

An optical construction of the variable magnification optical system will be described below. As described above, the variable magnification optical system includes a first lens group arranged closest to an observation optical system side, a final lens group arranged closest to an image side, and a plurality of movable lens groups arranged between the first lens group and the final lens group and movable in an optical axis direction.

In the variable magnification optical system, the first lens group and the final lens group are fixed in the optical axis direction, and the plurality of movable lens groups are moved in the optical axis direction, to change (e.g., enlarge) a magnification of an object image formed by a rigid endoscope, for example. In the variable magnification optical system, an observation magnification of an affected site can arbitrarily be changed by adjusting an amount of movement or the like of each of the movable lens groups to continuously adjust an imaging field of view (observation image viewing angle). Accordingly, at the time of endoscopic surgery using a rigid endoscope image display system, for example, enlarged observation, partial observation, or the like of the affected site can arbitrarily be performed in keeping with the progress of the surgery. In the case, a distance between a distal end of the insertion section in the rigid endoscope (to be precise, a distal end of an objective lens) and the affected site (an object), i.e., a working distance of the rigid endoscope need not be changed. Therefore, an observation field of view and an observation magnification can be adjusted to those required in keeping with the progress of the operation while the distal end of the insertion section in the rigid endoscope is arranged at a position that does not interfere with surgical instruments or the like. Further, a zooming mechanism need not be provided on a rigid endoscope side. Thus, it is possible to simplify the optical construction of the rigid endoscope, and prevent the increase in size of the rigid endoscope, particularly the insertion section. Note that, the zooming mechanism refers to a movable lens group provided to change an observation magnification of the object image, a driving mechanism such as a cam for moving the movable lens group in the optical axis direction, or the like.

In the variable magnification optical system, at least one of the above-described plurality of movable lens groups is moved in the optical axis direction to perform focusing on a nearest point object from a farthest point object. Accordingly, when the observation field of view and/or the observation magnification are/is changed, the affected site to be observed can be brought into focus, and an object image having a high resolution can be obtained.

In the variable magnification optical system, the number of movable lens groups may be at least two between the first lens group and the final lens group. With two movable lens groups, it is possible to continuously change an observation magnification of the object image by moving the two movable lens groups in the optical axis direction at the time of zooming. At the time of focusing, by moving at least one of the lens groups, it is possible to perform the focusing.

Accordingly, a focusing mechanism need not be provided on the rigid endoscope side so that an optical construction of the rigid endoscope can be simplified. Therefore, it is possible to prevent the increase in size of the rigid endoscope from this viewpoint as well. Note that, the focusing mechanism referred to herein means a movable lens group provided to adjust a focusing position and a driving mechanism such as a cam for moving the movable lens group in the optical axis direction.

Further, in the variable magnification optical system, the first lens group arranged closest to the observation optical system side and the final lens group arranged closest to the image side are fixed in the optical axis direction at the time of zooming and at the time of focusing. Thus, an optical overall length of the variable magnification optical system does not change at the time of zooming and at the time of focusing. The variable magnification optical system is housed in the lens barrel, and is constructed as a lens unit. When the optical overall length is fixed, a length of the lens barrel that houses the variable magnification optical system can also be fixed. Thus, a lens barrel structure can be simplified. Accordingly, the lens unit is easily made to have a watertight structure, a waterproof structure, or a sealed structure capable of disinfection, bacteria elimination, sterilization, and the like of the lens unit.

The variable magnification optical system should preferably include a negative movable lens group having negative refractive power and a positive movable lens group having positive refractive power in this order from the above-described ocular section side between the first lens group and the final lens group. In the embodiment, the variable magnification optical system is used while being connected to the ocular section in the observation optical system. Under such a condition, external light does not directly enter the variable magnification optical system, and the variable magnification optical system is virtually equipped with a stop having a prescribed aperture diameter defined by the rigid endoscope on the ocular section side in the first lens group. In such a case, when the negative movable lens group having negative refractive power and the positive movable lens group having positive refractive power are arranged as the movable lens groups in this order from the above-described ocular section side, it is possible to arbitrarily select the observation image viewing angle and the working distance, favorably perform a spherical aberration, and miniaturize the variable magnification optical system.

In this case, the negative movable lens group should preferably be moved in the optical axis direction to perform focusing on the nearest point object from the farthest point object. When the negative movable lens group is thus used as a zooming group to be moved at the time of zooming while being used as a focusing group to be moved at the time of focusing, it is possible to simplify the optical construction of the variable magnification optical system, and also simplify the driving mechanism. As a result, the above-described lens unit can be miniaturized and made lightweight.

Although respective signs of the refractive powers provided in the first lens group and the final lens group are not particularly limited in the variable magnification optical system, the first lens group should preferably have positive refractive power and the final lens group should preferably have negative refractive power when the variable magnification optical system is constructed to include the negative movable lens group and the positive movable lens group, described above. That is, when the variable magnification optical system is constructed to include the first lens group having positive refractive power, the negative movable lens group, the positive movable lens group, and the final lens group having negative refractive power in the order from the ocular section side, the observation image viewing angle and the working distance can arbitrarily be selected, and a compact variable magnification optical system having high optical performance can be easily realized. Note that, another fixed lens group or movable lens group may be arranged between the negative movable lens group and the positive movable lens group. In this case, the other fixed lens group or movable lens group should preferably have positive refractive power. The larger the number of lens groups is, the more preferable it is in favorably performing abrasion correction while making a zoom ratio high. However, that is not preferable in miniaturizing the magnification optical system because a mechanical structure of the variable magnification optical system becomes complicated.

In the variable magnification optical system having the above-described construction, image blurring such as handshake blurring occurred at the time of imaging may be corrected by constructing the final lens group to be movable in a direction perpendicular to the optical axis and moving the final lens group in the direction perpendicular to the optical axis. That is, the final lens group may be constructed as a so-called vibration-compensation group.

Further, in the variable magnification optical system, respective outer diameters of lenses included in the first lens group should preferably be smaller than respective outer diameters of lenses included in the final lens group. More specifically, the outer diameter of the lens having the largest diameter among the lenses included in the first lens group should preferably be smaller than the outer diameter of the lens having the smallest diameter among the lenses included in the final lens group. The rigid endoscope is constructed by the lens having a small diameter because it is inserted into a narrow portion such as the inside of a body. Since the variable magnification optical system is thus constructed, the variable magnification optical system can be appropriately connected to the rigid endoscope having a small diameter while a rigid endoscope image can be favorably formed on an image plane while the variable magnification optical system is miniaturized and made lightweight.

1-3. Conditional Expressions

Next, conditions that should preferably be satisfied by the variable magnification optical system will be described.

1-3-1. Conditional Expression (1)

The variable magnification optical system should preferably satisfy the following condition:

$$bt \leq -0.80 \quad (1)$$

where bt: a maximum imaging magnification at a telephoto end of the variable magnification optical system.

Conditional expression (1) is an expression for defining an upper-limit value of a maximum imaging magnification at the telephoto end of the variable magnification optical system, i.e., a maximum imaging magnification in a minimum imaging distance of the variable magnification optical system. At this time, the imaging magnification refers to a ratio of a height of an image plane (an image height) to a height of an object. When conditional expression (1) is satisfied, it is possible to form an image of the object (an object image) in a size that is 0.8 times the actual size of the object on the image plane by the variable magnification optical system. Accordingly, by constructing the variable magnification optical system like a micro lens having a short minimum imaging distance, it is possible to shorten the minimum imaging distance of the rigid endoscope also when the ocular section in the rigid endoscope and the variable magnification optical system are connected to each other so that an affected site can be observed in a more enlarged manner. In a conventional example, when biopsies of a tissue in the vicinity of an affected site are required, the tissue in the vicinity of the affected site needs to be collected and taken out of a body, and be separately observed by a microscope, to judge whether or not the tissue is a cancer cell, for example. However, when the variable magnification optical system is connected to the ocular section in the rigid endoscope, an observation magnification of the rigid endoscope can be made equal to or more than that of the microscope, and the affected site and the vicinity of the affected site can be directly observed in an enlarged manner while changing an observation field of view without the tissue in the vicinity of the affected site being collected and observed outside the body. Accordingly, a doctor can appropriately and quickly determine a region to be resected while confirming a boundary portion between a normal tissue and a diseased tissue anytime during surgery, and can perform accurate surgery that imposes less stress on a patient.

The variable magnification optical system can be used alone as an imaging optical system without being connected to the ocular section in the rigid endoscope, as described above. In the case, the variable magnification optical system can be used as a macro-zoom lens.

In obtaining the above-described effect, the upper-limit value defined by conditional expression (1) is more preferably −0.90, and still more preferably −1.00. Note that, it is also preferable to set conditional expression (1) to bt<−0.80, bt<−0.90, and bt<−1.00. Although there is no particular optical meaning in providing a lower-limit value defined by above-described conditional expression (1), the lower-limit value may be set to approximately −10.0 or approximately −5.0. When the lower-limit value defined by conditional expression (1) is less than −10.0 or less than −5.0, an amount of movement of the focusing group increases. Thus, the optical overall length of the variable magnification optical system unpreferably increases.

1-3-2. Conditional Expression (2)

The variable magnification optical system should preferably satisfy the following condition:

$$1.00 \leq bit \leq 3.00 \quad (2)$$

where bit: a lateral magnification of the final lens group at the time of focusing on the farthest point object at the telephoto end.

Conditional expression (2) is an expression for defining a range of the lateral magnification of the final lens group at the time of focusing on the farthest point object at the telephoto end. Satisfying conditional expression (2) makes it possible to easily make the variable magnification optical system as a bright optical system having a small F number, and also to favorably correct spherical aberration. Further, it is also effective in achieving a reduction in size of the variable magnification optical system.

On the other hand, when a numerical value of conditional expression (2) is less than the lower-limit value, the lateral magnification of the final lens group at the time of focusing on the farthest point object at the telephoto end is too small. Thus, a focal length of a system composed of lens groups from the first lens group to the lens group arranged on the object side of the final lens group increases so that an optical overall length increases, which is not preferable in miniaturizing the variable magnification optical system. On the other hand, when the numerical value of conditional expression (2) exceeds an upper-limit value, the lateral magnification of the final lens group at the time of focusing on the farthest point object at the telephoto end becomes too large. Therefore, it is difficult to decrease the F number, and is undesirable because a bright optical system cannot be realized.

In obtaining the above-described effect, the lower-limit value defined by conditional expression (2) is more preferably 1.10, still more preferably 1.20, and much more preferably 1.30. The upper-limit value defined by conditional expression (2) is more preferably 2.60, still more preferably 2.40, much more preferably 2.20, and further much more preferably 2.00.

1-3-3. Conditional Expression (3)

When the variable magnification optical system is constructed to include the negative movable lens group having negative refractive power and the positive movable lens group having positive refractive power in this order from the ocular section side between the first lens group and the final lens group, as described above, the following condition should preferably be satisfied:

$$0.40 \leq mn/mp \leq 2.00 \tag{3}$$

where mn: an amount of movement in the optical axis direction of the negative movable lens group at the time of zooming from the wide angle end to the telephoto end (a sign is made positive for movement toward the image side), and mp: an amount of movement in the optical axis direction of the positive movable lens group at the time of zooming from the wide angle end to the telephoto end (a sign is made positive for movement toward the image side).

Conditional expression (3) is an expression for defining a ratio of an amount of movement in the optical axis direction of the negative movable lens group at the time of zooming to an amount of movement in the optical axis direction of the positive movable lens group at the time of zooming. Note that, the time of zooming refers to the time when a magnification is changed from the wide angle end to the telephoto end. Satisfying conditional expression (3) means that the negative movable lens group and the positive movable lens group move in the same direction along the optical axis. By setting the movements of the positive movable lens group as a second lens group and the negative movable lens group as a third lens group in the same direction while the ratio of the movement amounts is set within the range of conditional expression (3), it is possible to prevent the optical overall length of the variable magnification optical system from increasing while securing respective amounts of movement of both the movable lens groups and realizing a high zoom ratio.

On the other hand, when a numerical value of conditional expression (3) is less than the lower-limit value, the amount of movement of the negative movable lens group becomes too small with respect to the amount of movement of the positive movable lens group. If the direction of movement is toward the image side, it is difficult to make the variable magnification optical system as a variable magnification optical system having a high zoom ratio. On the other hand, when the numerical value of conditional expression (3) exceeds the upper-limit value, the amount of movement of the negative movable lens group becomes too large with respect to the amount of movement of the positive movable lens group. If the direction of the movement is toward the image side, in general, the negative movable lens group is moved toward the image side at the telephoto end, or the positive movable lens group is moved toward the object side, to perform focusing on the nearest point object from the farthest point object. When a distance between the negative movable lens group and the positive movable lens group is short at the telephoto end, it is not possible to secure an amount of movement of the negative movable lens group at the time of focusing. The distance between the negative movable lens group and the positive movable lens group needs to be secured at the telephoto end to secure the amount of movement of the negative movable lens group at the time of focusing. Therefore, the optical overall length of the variable magnification optical system unpreferably increases.

In obtaining the above-described effect, the lower-limit value defined by conditional expression (3) is more preferably 0.50, and still more preferably 0.55. The upper-limit value is more preferably 1.80, still more preferably 1.60, and much more preferably 1.40.

1-3-4. Conditional Expression (4)

The variable magnification optical system should preferably satisfy the following condition:

$$0.20 \leq |fi|/\sqrt{(fw \times ft)} \leq 1.20 \tag{4}$$

where fi: a focal length of the final lens group, fw: a focal length of the entire variable magnification optical system at the time of focusing on the farthest point object at the wide angle end, and ft: a focal length of the entire variable magnification optical system at the time of focusing on the farthest point object at the telephoto end.

Note that, "$\sqrt{(fw \times ft)}$" represents a focal length of the variable magnification optical system at an intermediate focal length position (hereinafter referred to as an "intermediate focal length"). Conditional expression (4) is an expression for defining a ratio of the focal length of the final lens group to the intermediate focal length of the variable magnification optical system. When conditional expression (4) is satisfied, it is possible to reduce aberrations generated in the final lens group. Accordingly, when the final lens group is constructed to be movable in the direction perpendicular to the optical axis and is constructed to be moved in the direction perpendicular to the optical axis as a vibration-compensation group, to correct image blurring, it is possible to reduce decentration coma aberration, decentration astigmatism, and decentration chromatic aberration when the final lens group is moved in the direction perpendicular to the optical axis. Accordingly, a good optical performance can also be obtained with a small number of lenses at the time of vibration compensation, and the variable magnification optical system can also be constructed in a small size even when a vibration-compensation function is provided. The amount of movement in the direction perpendicular to the optical axis of the final lens group at the time of vibration compensation can also be set in an appropriate range. Thus, it is also possible to prevent a diameter of the lens barrel that houses the variable magnification optical system from increasing.

On the other hand, if a numerical value of conditional expression (4) is less than the lower-limit value, the refractive power of the final lens group becomes too strong. Thus, it is difficult to use the final lens group as a vibration-compensation group. That is, decentration coma aberration, decentration astigmatism, and decentration chromatic aberration increase when the final lens group is moved in the direction perpendicular to the optical axis. Accordingly, to maintain a good optical performance, a large number of lenses are required for aberration correction. Therefore, the final lens group becomes large and heavy by an increase in the number of lenses, which is not preferable in miniaturizing the variable magnification optical system. When the vibration-compensation group becomes heavy, the driving mechanism for driving the vibration-compensation group also unpreferably increases in size. On the other hand, when the numerical value of conditional expression (4) exceeds the upper-limit value, the refractive power of the final lens group becomes too weak. Thus, to secure a vibration-compensation correction angle, an amount of movement in the direction perpendicular to the optical axis of the final lens group at the time of vibration compensation needs to be increased. Therefore, in this case, the diameter of the lens barrel that houses the variable magnification optical system needs to be increased, which is not preferable in miniaturizing the above-described lens unit.

In obtaining the above-described effect, the lower-limit value defined by conditional expression (4) is more preferably 0.30, and still more preferably 0.40. The upper-limit value defined by conditional expression (4) is more preferably 1.00, still more preferably 0.90, and much more preferably 0.80.

2. Imaging Apparatus

Next, an imaging apparatus according to the present invention will be described. The imaging apparatus according to the present invention is characterized by including the above-described variable magnification optical system and an image sensor that converts into an electrical signal an optical image (object image) formed by the variable magnification optical system on the image side thereof. Note that, although there is no particular limitation on the image sensor or the like, the variable magnification optical system according to the present invention is appropriate for a solid-state image sensor having a high resolution and having a large image height. Thus, the resolution of the solid-state image sensor should preferably be not less than a resolution of full hi-definition, more preferably not less than a resolution of 4K, and still more preferably not less than a resolution of 8K.

The imaging apparatus may be constructed as a digital still camera that acquires a still image, or may be constructed as a digital video camera that acquires a movie. In the above-described variable magnification optical system, when the above-described negative movable lens group is used as a focusing group, for example, it is possible to perform quick focusing. Accordingly, with the variable magnification optical system according to the present invention, it is possible to favorably observe the object to the fine detail when the object image is displayed in an enlarged manner on the display device while the observation magnification and the observation field of view are changed as needed. Therefore, even when quick and accurate judgment corresponding to a situation of an affected site, for example, is required, like in endoscopic surgery, it is possible to provide accurate information i.e., information about the details of the object, for making a judgement, by connecting the imaging apparatus to the ocular section in the rigid endoscope. Note that, the imaging apparatus may be a fixed lens imaging apparatus in which the above-described variable magnification optical system is fixed to a housing or may be an interchangeable-lens imaging apparatus in which the variable magnification optical system is removably constructed.

3. Observation Image Display System

Next, a rigid endoscope image display system (observation image display system) to which the variable magnification optical system and the imaging apparatus according to the present invention are applied will be described. The rigid endoscope image display system should preferably include an image processing section that electrically processes image data relating to an optical image generated by the variable magnification optical system. The image processing section may be provided in a main body of the above-described imaging apparatus, or may be provided in a control device (e.g., a personal computer) that controls an image display operation of the display device.

In the above-described variable magnification optical system according to the present invention, when a high-resolution compact optical system is desired to be obtained while a high zoom ratio is realized, an image shape becomes susceptible to distortion. By providing the observation image display system with an image processing section that electrically processes the distortion of the image shape for the above-described image data, it is possible to output an observation object image whose image shape is hardly distorted to an image output device or the like. Note that, the image processing section should preferably include a storage section that has correction data for correcting the distortion of the image shape stored in advance, a central processing unit (CPU) that corrects image data acquired in an observation imaging apparatus in association with the correction data.

Note that, the above-described image processing section should preferably electrically process data relating to distortion aberration out of image data relating to an optical image formed by the variable magnification optical system. In the image processing section, when the data relating to the distortion aberration can be electrically processed, it is possible to display an observation object image on the image output device or the like without distortion even if strong refractive power is provided while the negative movable lens group in the above-described variable magnification optical system is composed of lenses each having a small diameter.

The above-described image processing section should preferably electrically process image data relating to magnification chromatic aberration out of image data relating to an optical image formed by the variable magnification optical system. In the image processing section, when the data relating to the magnification chromatic aberration can be electrically processed, it is possible to display an object image with small chromatic aberration on the image output device or the like. Accordingly, the number of lenses composing the variable magnification optical system can be reduced so that the variable magnification optical system can be easily miniaturized.

Next, the present invention will be specifically described by way of examples. Note that, the present invention is not limited to the following examples. The optical system in each of the examples cited below is an observation optical system as an imaging optical system used for an imaging apparatus (optical apparatus) such as a digital camera or a video camera, and particularly can be preferably applied to a microscope or an observation imaging apparatus for performing internal observation of a narrow space. In the cross-sectional view of each lens, the left side of the drawing is the observation object side (an object side or an observation optical system side) and the right side is the image side.

Example 1

Examples of the variable magnification optical system according to the present invention will be described with reference to the drawings. FIG. 1 is a diagram illustrating a lens construction example of a variable magnification optical system in an example 1, where an upper part is a lens construction diagram in a wide angle end state, and a lower part is a lens construction diagram in a telephoto end state.

As illustrated in FIG. 1, the variable magnification optical system in Example 1 includes a first lens group G1 having positive refractive power, a second lens group G2 having negative refractive power, a third lens group G3 having positive refractive power, and a fourth lens group G4 having negative refractive power in this order from the object side. The variable magnification optical system is used while being connected to an ocular section in a rigid endoscope not illustrated. Note that, the specific lens construction of each of the lens groups is as illustrated in FIG. 1. In FIG. 1, "S" illustrated on the object side of the first lens group G1 represents a virtual stop position when the ocular section in the rigid endoscope is connected to the first lens group G1. "CG" refers to a cover glass, a low-pass filter, an infrared filter, or the like. "I" refers to an image plane, and represents an imaging plane of a solid-state image sensor such as a CCD sensor or a CMOS sensor or a film surface of a silver-halide film, for example. These points are similar to those in the cross-sectional view of each lens illustrated in other examples, and hence description thereof is omitted hereinafter.

When zooming from a wide angle end to a telephoto end, the first lens group G1 and the fourth lens group G4 are fixed in the optical axis direction, and the second lens group G2 and the third lens group G3 respectively move toward the image side through different trajectories. At the time of focusing on a nearest point object from a farthest point object, the second lens group G2 moves toward the image side. The fourth lens group G4 is constructed to be movable in a direction perpendicular to the optical axis. By moving the fourth lens group G4 in the direction perpendicular to the optical axis, it is possible to correct image blurring such as hand-shake blurring occurred at the time of imaging.

Note that, in the variable magnification optical system in Example 1, the second lens group G2 is a negative movable lens group for in the present invention, the third lens group G3 is a positive movable lens group, and the fourth lens group G4 is a final lens group.

Figure 2:
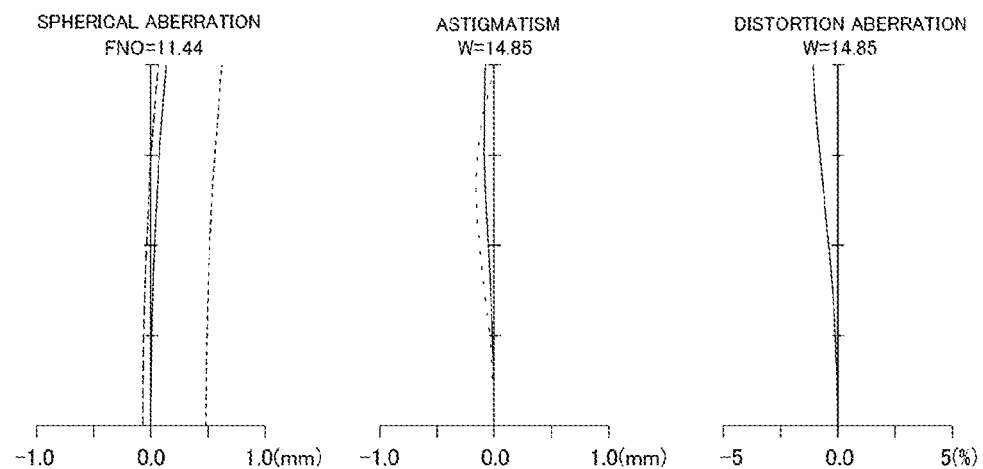
FIG. 2 illustrates spherical aberration, astigmatism, and distortion aberration at the time of focusing on a farthest point object in a wide angle end state of the variable magnification optical system in Example 1 of the present invention.
Figure 3:
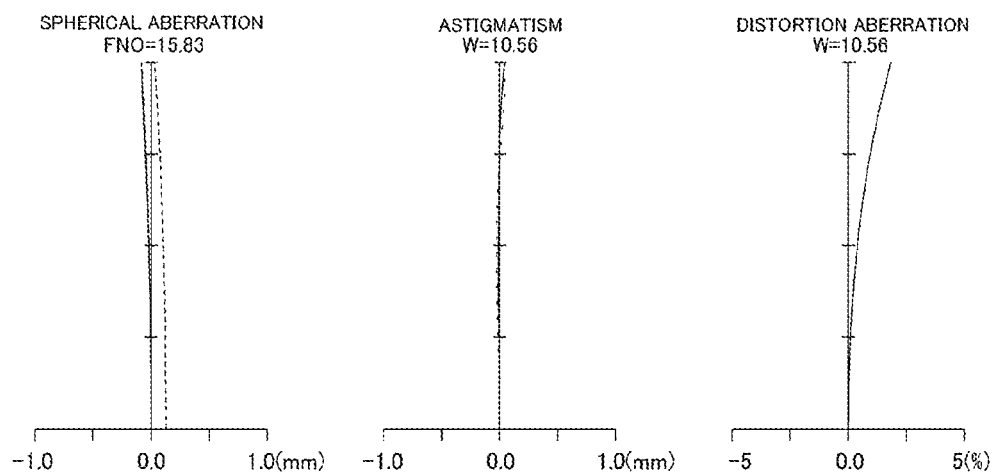
FIG. 3 illustrates spherical aberration, astigmatism, and distortion aberration at the time of focusing on the farthest point object at an intermediate focus point of the variable magnification optical system in Example 1 of the present invention.
Figure 4:
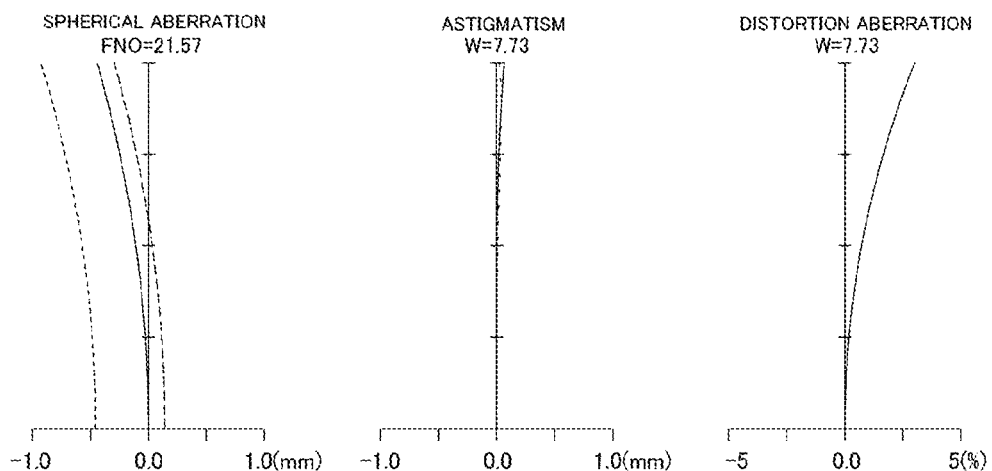
FIG. 4 illustrates spherical aberration, astigmatism, and distortion aberration at the time of focusing on the farthest point object in a telephoto end state of the variable magnification optical system in Example 1 of the present invention.

FIG. 2 to FIG. 4 each illustrate spherical aberration, astigmatism, and distortion aberration at the time of infinity focusing in a wide angle end state, an intermediate focal length state, and a telephoto end state of the variable magnification optical system in Example 1. In each spherical aberration diagram, the vertical axis represents an F number (indicated by FNO in the drawing), the solid line represents a characteristic of a d line (a wavelength λ=587.56 nm), the short broken line represents a characteristic of a g line (a wavelength λ=435.84 nm), and the long broken line represents a characteristic of a C line (a wavelength λ=656.27 nm). In each astigmatism diagram, the vertical axis represents an image viewing angle (indicated by W in the drawing), the solid line represents a characteristic of a sagittal plane, and the broken line represents a characteristic of a meridional plane. In each distortion aberration diagram, the vertical axis represents an image viewing angle (indicated by W in the drawing). These characteristics are the characteristics of the variable magnification optical system itself, and are characteristics of the variable magnification optical system used alone without being connected to the ocular section in the rigid endoscope. The same applies to lateral aberration described below.

Figure 5:
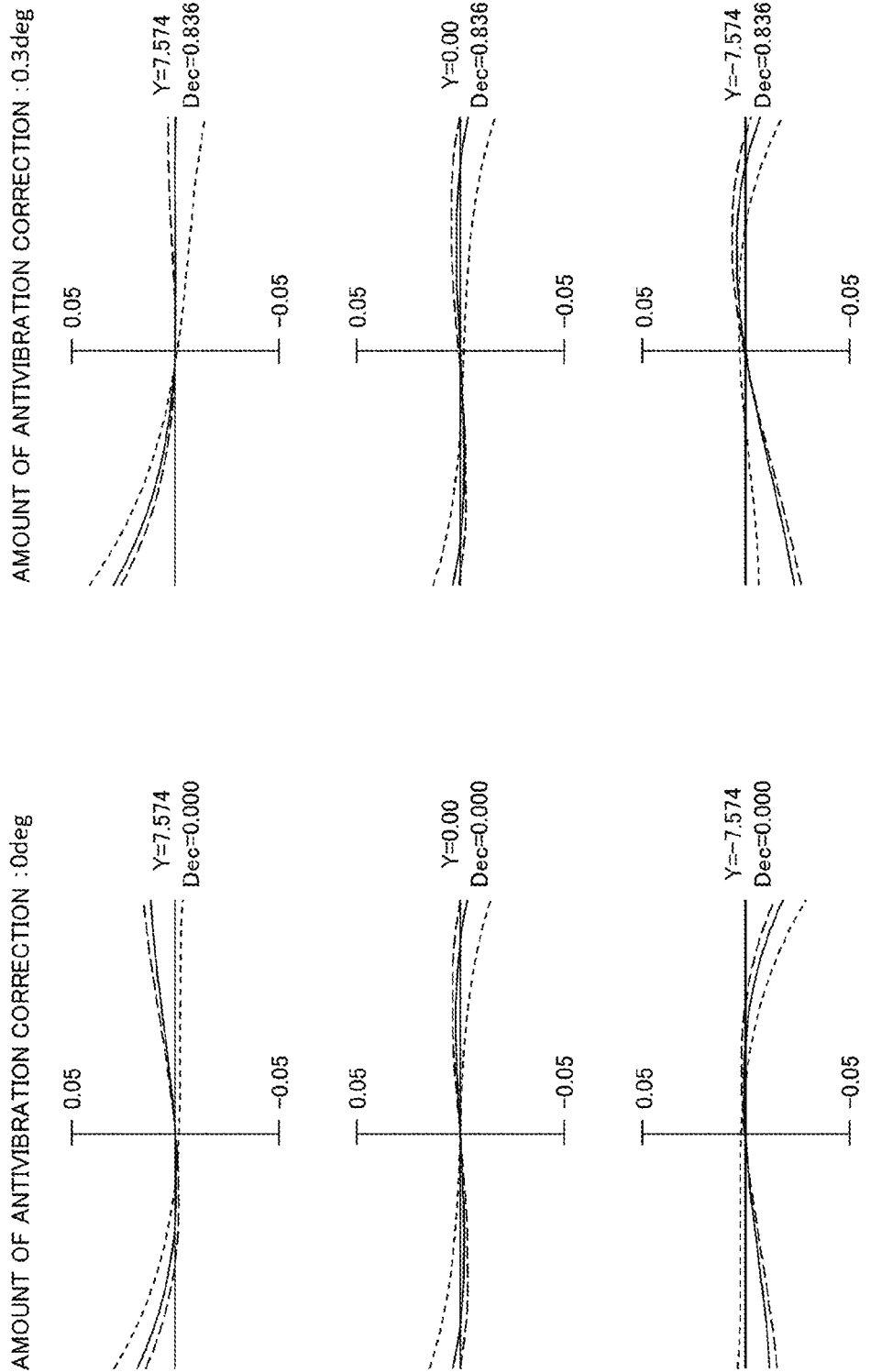
FIG. 5 is a lateral aberration diagram in the telephoto end state of the variable magnification optical system in Example 1 of the present invention.

FIG. 5 illustrates lateral aberration diagrams at the telephoto end of the variable magnification optical system in Example 1. In each of the lateral aberration diagrams illustrated in FIG. 5, the three aberration diagrams positioned on the left side of the figure correspond to a basic state where hand-shake correction at the telephoto end has not been performed (amount of vibration-compensation correction 0 deg.). The three aberration diagrams positioned on the right side of the figure correspond to a hand-shake correction state at the telephoto end where the fourth lens group as a vibration-compensation group has been moved by a prescribed amount in the direction perpendicular to the optical axis, where dec represents an amount of movement of the vibration-compensation group.

In each of the lateral aberration diagrams of the basic state, the top part corresponds to lateral aberration at an image point of 70% of the maximum image height, the middle part corresponds to lateral aberration at an image point on the axis, and the bottom part corresponds to lateral aberration at an image point of −70% of the maximum image height. In each of the lateral aberration diagrams corresponding to the hand-shake correction state, the top part corresponds to lateral aberration at an image point of 70% of the maximum image height, the middle part corresponds to lateral aberration at an image point on the axis, and the bottom part corresponds to lateral aberration at an image point of −70% of the maximum image height. In each of the lateral aberration diagrams, the horizontal axis represents a distance from a principal ray on a pupil plane, the solid line represents a characteristic of a d line, the short broken line represents a characteristic of a g line, and the long broken line represents a characteristic of a C line. For the variable magnification optical system, an amount of angle change by moving the vibration-compensation group by a prescribed amount in the direction perpendicular to the optical axis at the time of hand-shake correction is 0.3 degrees. An amount of movement of the vibration-compensation group at that time is 0.836 mm.

As is apparent from FIG. 5, it is understood that the symmetric property of the lateral aberration at the image point on the axis is good. When the lateral aberration at the image point of +70% and the lateral aberration at the image point of −70% are compared with each other in the basic state, respective degrees of curvature of the lateral aberrations are small, and respective slopes of the aberration curves are substantially equal to each other. Thus, it is understood that the decentration coma aberration and the decentration astigmatism are small. This means that satisfactory image forming performance is obtained even in the hand-shake correction state. At any zoom position, satisfactory hand-shake correction can be performed without degrading the image forming characteristics for a hand-shake correction angle up to 0.3 degrees. Further, when an amount of movement of the vibration-compensation group in the direction perpendicular to the optical axis is further increased, the hand-shake correction angle can also be increased to larger than 0.3 degrees. These points also apply to other examples described below.

Next, in Example 1, Table 1 illustrates lens data of numerical value example 1 to which specific numerical values are applied. The lens data illustrated in Table 1 are as follows. "Surface number" represents the order of lens surfaces counted from the object side, "r" represents the radius of curvature of the lens surface, "d" represents the lens thickness or the spacing on the optical axis between adjacent lens surfaces, "nd" represents the refractive index for the d line, and "vd" represents the Abbe number for the d line. In the column of "r", "∞" means that the radius of curvature is ∞ (infinite). The column designated as "dn (where n is a surface number)" such as "d5" described in a column of "d" indicates that the spacing is a variable spacing at the time of zooming. Note that, in each of the tables, the unit of length is "mm", and the unit of image viewing angle is "°".

Table 2 illustrates various types of data in the variable magnification optical system. Table 2 illustrates a "focal length", an "F number", a "half image viewing angle", a "total lens length (optical overall length)", and a "back focus" of the variable magnification optical system, and a variable spacing (note that, at the time of infinity focusing) "dn" on the optical axis at the time of zooming illustrated in Table 1 at the wide angle end, the intermediate focal length position, and the telephoto end. Table 2 also illustrates a zoom ratio and an image height of the variable magnification optical system.

Table 3 illustrates a "start surface" and a "focal length" of each of the lens groups composing the variable magnification optical system, a "construction length" corresponding to a length on the optical axis from the start surface to a final surface of each of the lens groups, and a "movement amount" on the optical axis of each of the lens groups at the time of zooming. Note that, a sign is made positive for movement toward the image side.

Table 4 illustrates respective lateral magnifications of each of the lens groups at the wide angle end, the intermediate focal length position, and the telephoto end, together with the start surface of the lens group.

Table 5 illustrates a maximum imaging magnification at the telephoto end of the variable magnification optical system and variable spacing on the optical axis at the time of focusing on the nearest point object at the telephoto end. Note that, the nearest point object means an object at a minimum imaging distance position of the variable magnification optical system.

Table 26 illustrates respective numerical values of above-described conditional expressions (1) to (4) in the variable magnification optical system.

Items associated with the drawings and the tables are similar to those in the other examples, and hence description thereof is omitted.

TABLE 1

| Surface number | r | d | nd | vd | |
|---|---|---|---|---|---|
| 1 | ∞ | 6.852 | | | (Aperture stop) |
| 2 | ∞ | 0.900 | 1.5233 | 54.52 | |
| 3 | ∞ | 0.200 | | | |
| 4 | 23.438 | 2.574 | 1.4970 | 81.61 | |
| 5 | −34.980 | d5 | | | |
| 6 | −15.067 | 0.700 | 2.0006 | 25.46 | |
| 7 | 31.443 | 1.338 | | | |
| 8 | −17.999 | 1.000 | 1.8340 | 37.35 | |
| 9 | −38.288 | 0.200 | | | |
| 10 | 139.047 | 3.726 | 1.8467 | 23.78 | |
| 11 | −16.084 | d11 | | | |
| 12 | 147.451 | 6.393 | 1.4970 | 81.61 | |
| 13 | −31.032 | 0.200 | | | |
| 14 | 43.037 | 8.056 | 1.4970 | 81.61 | |
| 15 | −29.313 | 1.500 | 1.8467 | 23.78 | |
| 16 | −64.148 | d16 | | | |
| 17 | −33.340 | 3.116 | 1.8467 | 23.78 | |
| 18 | −19.864 | 1.500 | 1.7725 | 49.62 | |
| 19 | 127.889 | 11.373 | | | |
| 20 | ∞ | 4.200 | 1.5168 | 64.20 | |
| 21 | ∞ | 1.000 | | | |

TABLE 2

Zoom ratio 1.884 Image height 10.820

| | Wide angle end | Intermediate focal position | Telephoto end |
|---|---|---|---|
| Focal length | 41.201 | 56.987 | 77.639 |
| F number | 11.445 | 15.830 | 21.566 |
| Half image viewing angle | 14.854 | 10.561 | 7.727 |
| Total lens length | 102.080 | 102.080 | 102.080 |
| Back focus | 15.139 | 15.139 | 15.139 |
| d5 | 2.402 | 8.706 | 12.209 |
| d11 | 25.167 | 27.134 | 32.435 |
| d16 | 19.683 | 11.413 | 2.608 |

TABLE 3

| Group | Start surface | Focal length | Lens construction length | Amount of lens movement |
|---|---|---|---|---|
| First lens group | 1 | 28.658 | 10.526 | 0.000 |
| Second lens group | 6 | −25.773 | 6.963 | 9.807 |
| Third lens group | 12 | 31.939 | 16.148 | 17.075 |
| Fourth lens group | 17 | −35.829 | 4.616 | 0.000 |

TABLE 4

| Group | Start surface | Wide angle end | Intermediate focal position | Telephoto end |
|---|---|---|---|---|
| First lens group | 1 | 0.000 | 0.000 | 0.000 |
| Second lens group | 6 | −5.151 | 19.820 | 5.365 |
| Third lens group | 12 | −0.189 | 0.068 | 0.338 |
| Fourth lens group | 17 | 1.479 | 1.484 | 1.495 |

TABLE 5

| Minimum imaging distance | d5 | d11 | Maximum imaging magnification |
|---|---|---|---|
| 90.000 | 24.274 | 20.370 | −1.026 |

Example 2

(1) Construction of Optical System

Figure 6:
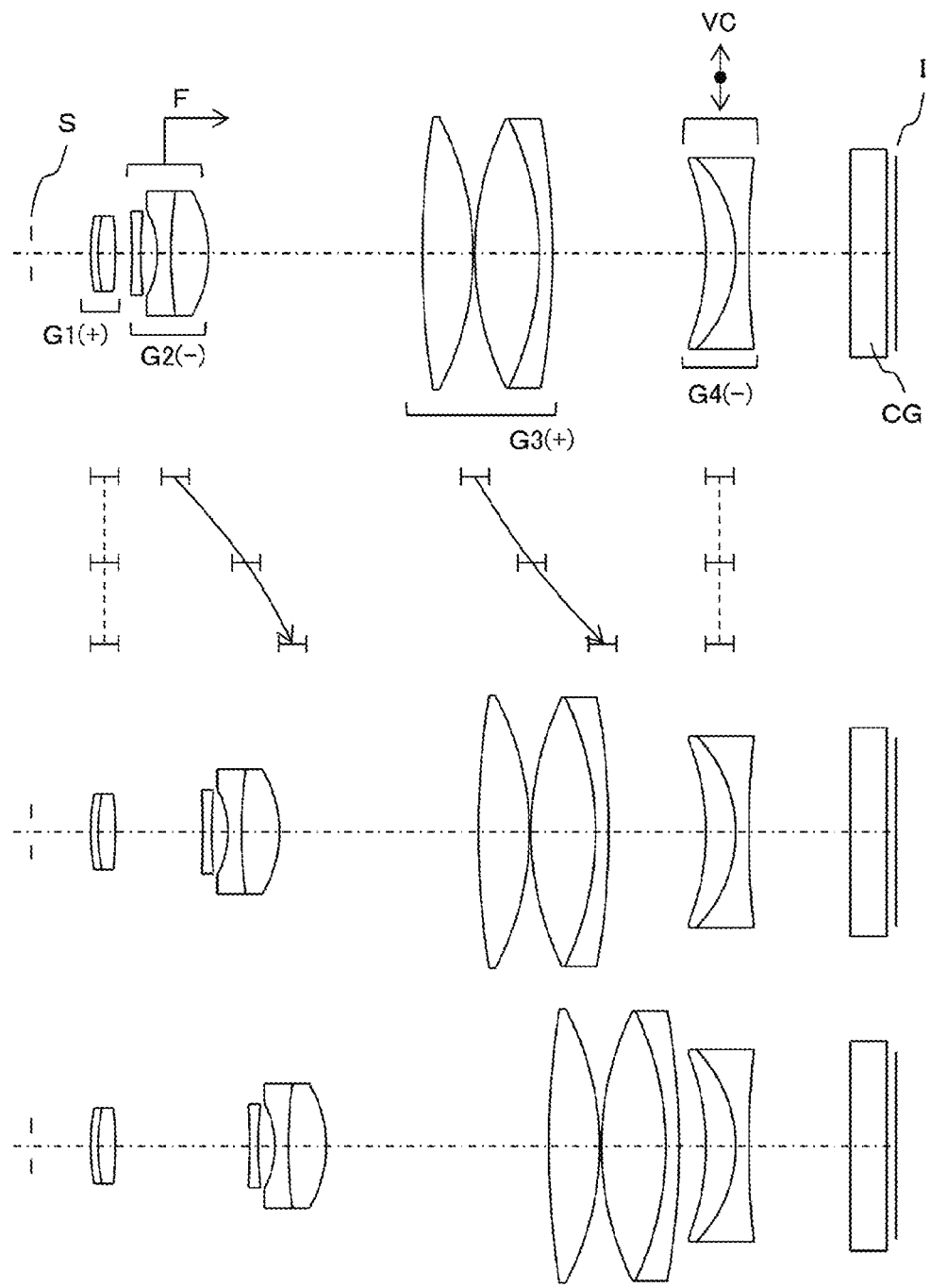
FIG. 6 is a diagram illustrating a lens construction example of a variable magnification optical system in Example 2 of the present invention, where the upper part is a lens construction diagram at a wide angle end, and the lower part is a lens construction diagram at a telephoto end.

FIG. 6 is a cross-sectional view illustrating a lens construction example of a variable magnification optical system in Example 2 according to the present invention. As illustrated in FIG. 6, the variable magnification optical system in Example 2 includes a first lens group G1 having positive refractive power, a second lens group G2 having negative refractive power, a third lens group G3 having positive refractive power, and a fourth lens group G4 having negative refractive power in this order from the object side. The variable magnification optical system is used while being connected to an ocular section in a rigid endoscope not illustrated. Note that, the specific lens construction of each of the lens groups is as illustrated in FIG. 6. Note that, the second lens group G2 is a negative movable lens group for the present invention, the third lens group G3 is a positive movable lens group, and the fourth lens group G4 is a final lens group.

When zooming from a wide angle end to a telephoto end, the first lens group G1 and the fourth lens group G4 are fixed in the optical axis direction, and the second lens group G2 and the third lens group G3 respectively move toward the image side through different trajectories. At the time of focusing on a nearest point object from a farthest point object, the second lens group G2 moves toward the image side. The fourth lens group G4 is constructed to be movable in a direction perpendicular to the optical axis. By moving the fourth lens group G4 in the direction perpendicular to the optical axis, it is possible to correct image blurring such as hand-shake blurring occurred at the time of imaging. An amount of movement of a vibration-compensation group is 0.779 mm when an amount of angle change by moving the vibration-compensation group by a prescribed amount in the direction perpendicular to the optical axis at the time of camera shake correction is set to 0.3 degrees.

(2) Numerical Value Examples

Next, numerical value examples to which specific numerical values of the variable magnification optical system are applied will be described. Table 6 illustrates surface data of the variable magnification optical system, Table 7 illustrates various types of data, Table 8 illustrates data relating to each of the lens groups composing the variable magnification optical system, Table 9 illustrates a lateral magnification or the like of each of the lens groups, and Table 10 illustrates a maximum imaging magnification or the like at the telephoto end of the variable magnification optical system. Table 26 illustrates the respective numerical values of above-described conditional expressions (1) to (4) in the variable magnification optical system.

Figure 7:
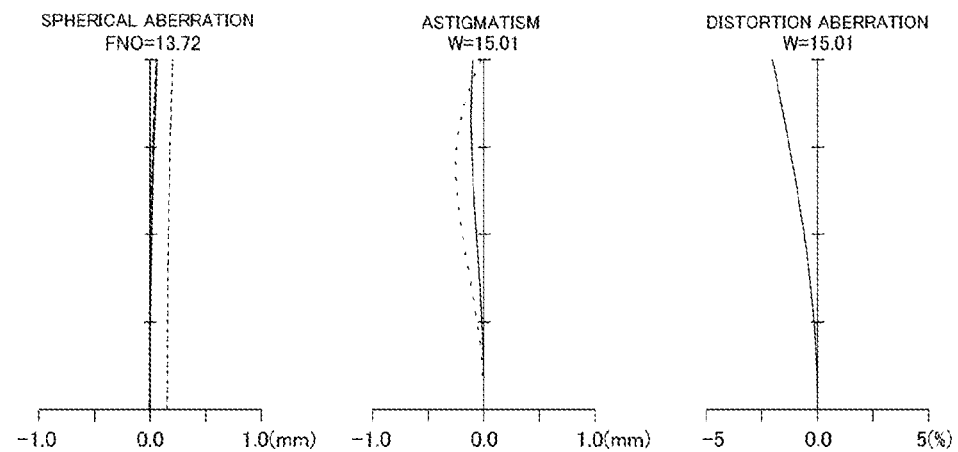
FIG. 7 illustrates spherical aberration, astigmatism, and distortion aberration at the time of focusing on a farthest point object in a wide angle end state of the variable magnification optical system in Example 2 of the present invention.
Figure 8:
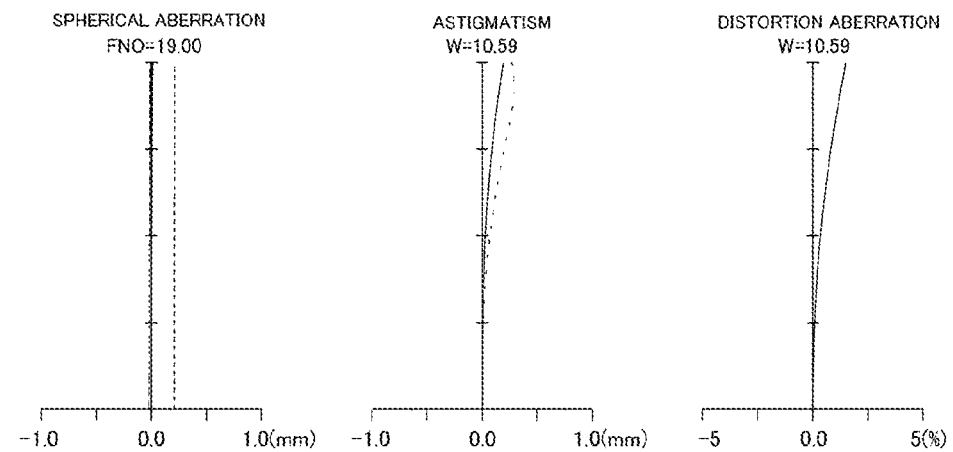
FIG. 8 illustrates spherical aberration, astigmatism, and distortion aberration at the time of focusing on the farthest point object at an intermediate focus point of the variable magnification optical system in Example 2 of the present invention.
Figure 9:
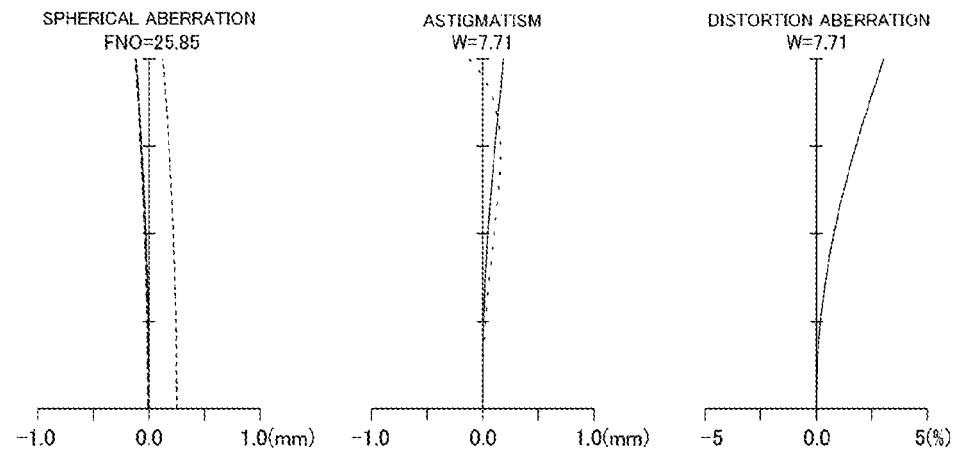
FIG. 9 illustrates spherical aberration, astigmatism, and distortion aberration at the time of focusing on the farthest point object in a telephoto end state of the variable magnification optical system in Example 2 of the present invention.
Figure 10:
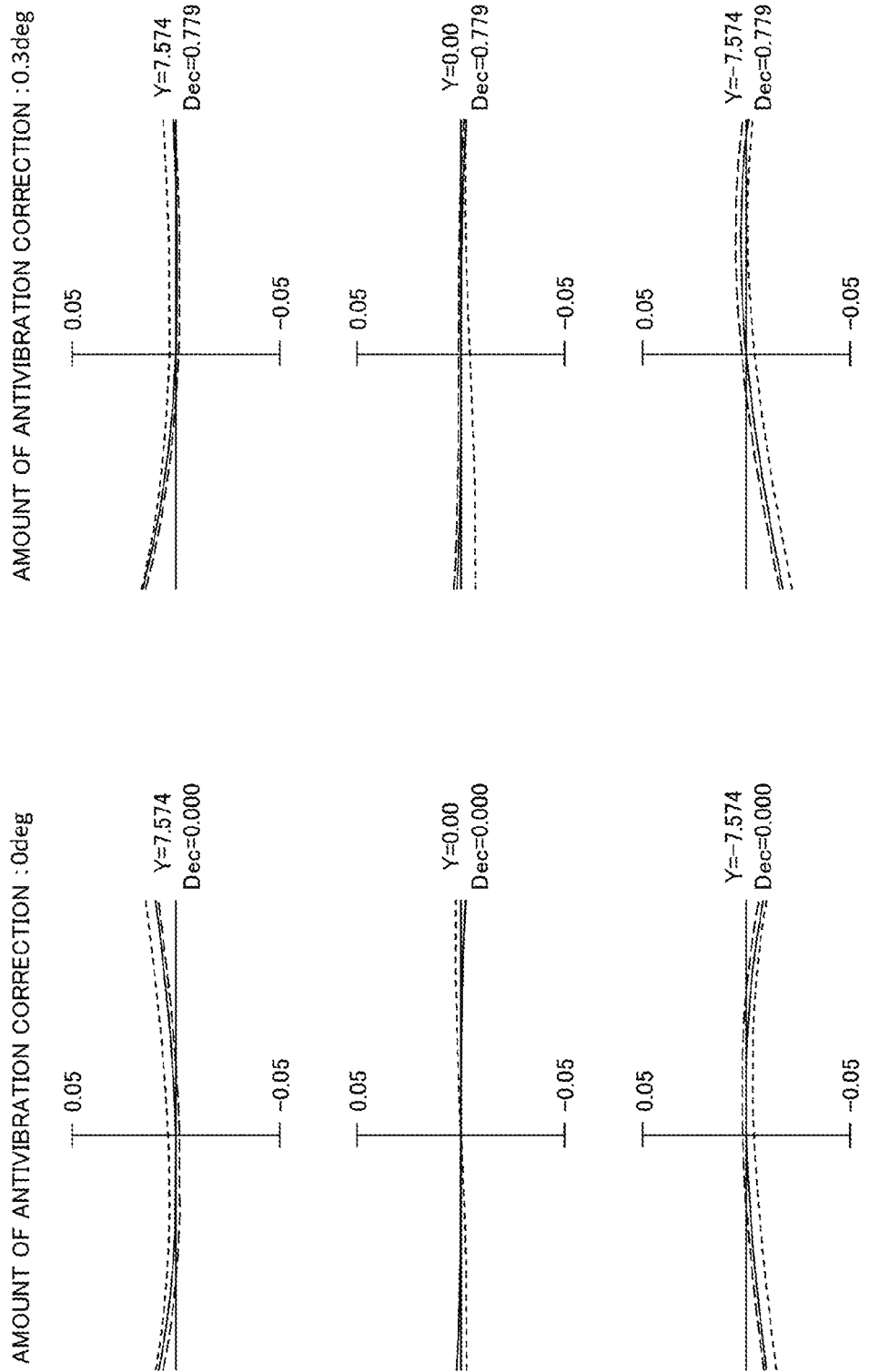
FIG. 10 is a lateral aberration diagram in the telephoto end state of the variable magnification optical system in Example 2 of the present invention.

FIG. 7 to FIG. 9 each illustrate spherical aberration, astigmatism, and distortion aberration at the time of infinity focusing in a wide angle end state, an intermediate focal length state, and a telephoto end state of the variable magnification optical system in Example 2. FIG. 10 illustrates lateral aberration diagrams at the telephoto end of the variable magnification optical system in Example 2.

TABLE 6

| Surface number | r | d | nd | vd | |
|---|---|---|---|---|---|
| 1 | ∞ | 6.852 | | | (Aperture stop) |
| 2 | 23.278 | 0.800 | 1.8467 | 23.78 | |
| 3 | 19.000 | 1.949 | 1.4970 | 81.61 | |
| 4 | −49.084 | d4 | | | |
| 5 | −112.313 | 1.000 | 1.8348 | 42.72 | |
| 6 | 46.171 | 1.906 | | | |
| 7 | −10.095 | 1.500 | 1.8061 | 33.27 | |
| 8 | 48.626 | 4.298 | 1.7408 | 27.76 | |
| 9 | −13.729 | d9 | | | |
| 10 | 99.898 | 5.752 | 1.4970 | 81.61 | |
| 11 | −32.513 | 0.200 | | | |
| 12 | 34.340 | 7.321 | 1.4970 | 81.61 | |
| 13 | −34.801 | 1.500 | 1.8467 | 23.78 | |
| 14 | −85.464 | d14 | | | |
| 15 | −27.869 | 3.373 | 1.8467 | 23.78 | |
| 16 | −15.115 | 1.500 | 1.7234 | 37.99 | |
| 17 | 102.739 | 11.470 | | | |
| 18 | ∞ | 4.200 | 1.5168 | 64.20 | |
| 19 | ∞ | 1.000 | | | |

TABLE 7

Zoom ratio 1.884, Image height 10.820

| | Wide angle end | Intermediate focal position | Telephoto end |
|---|---|---|---|
| Focal length | 41.158 | 56.997 | 77.548 |
| F number | 13.720 | 18.999 | 25.849 |
| Half image viewing angle | 15.013 | 10.590 | 7.712 |
| Total lens length | 98.109 | 98.109 | 98.109 |
| Back focus | 15.236 | 15.236 | 15.236 |
| d4 | 1.922 | 9.924 | 15.232 |
| d9 | 24.236 | 22.607 | 25.282 |
| d14 | 17.400 | 11.027 | 3.044 |

TABLE 8

| Group | Start surface | Focal length | Lens construction length | Amount of lens movement |
|---|---|---|---|---|
| First lens group | 1 | 35.736 | 9.531 | 0.000 |
| Second lens group | 5 | −28.851 | 8.704 | 13.311 |
| Third lens group | 10 | 29.600 | 14.773 | 14.356 |
| Fourth lens group | 15 | −34.084 | 4.873 | 0.000 |

TABLE 9

| Group | Start surface | Wide angle end | Intermediate focal position | Telephoto end |
|---|---|---|---|---|
| First lens group | 1 | 0.000 | 0.000 | 0.000 |
| Second lens group | 5 | −3.844 | 58.009 | 4.969 |
| Third lens group | 10 | −0.197 | 0.018 | 0.287 |
| Fourth lens group | 15 | 1.520 | 1.520 | 1.521 |

TABLE 10

| Minimum imaging distance | d4 | d9 | Maximum imaging magnification |
|---|---|---|---|
| 90.000 | 36.880 | 3.633 | −1.080 |

Example 3

(1) Construction of Optical System

Figure 11:
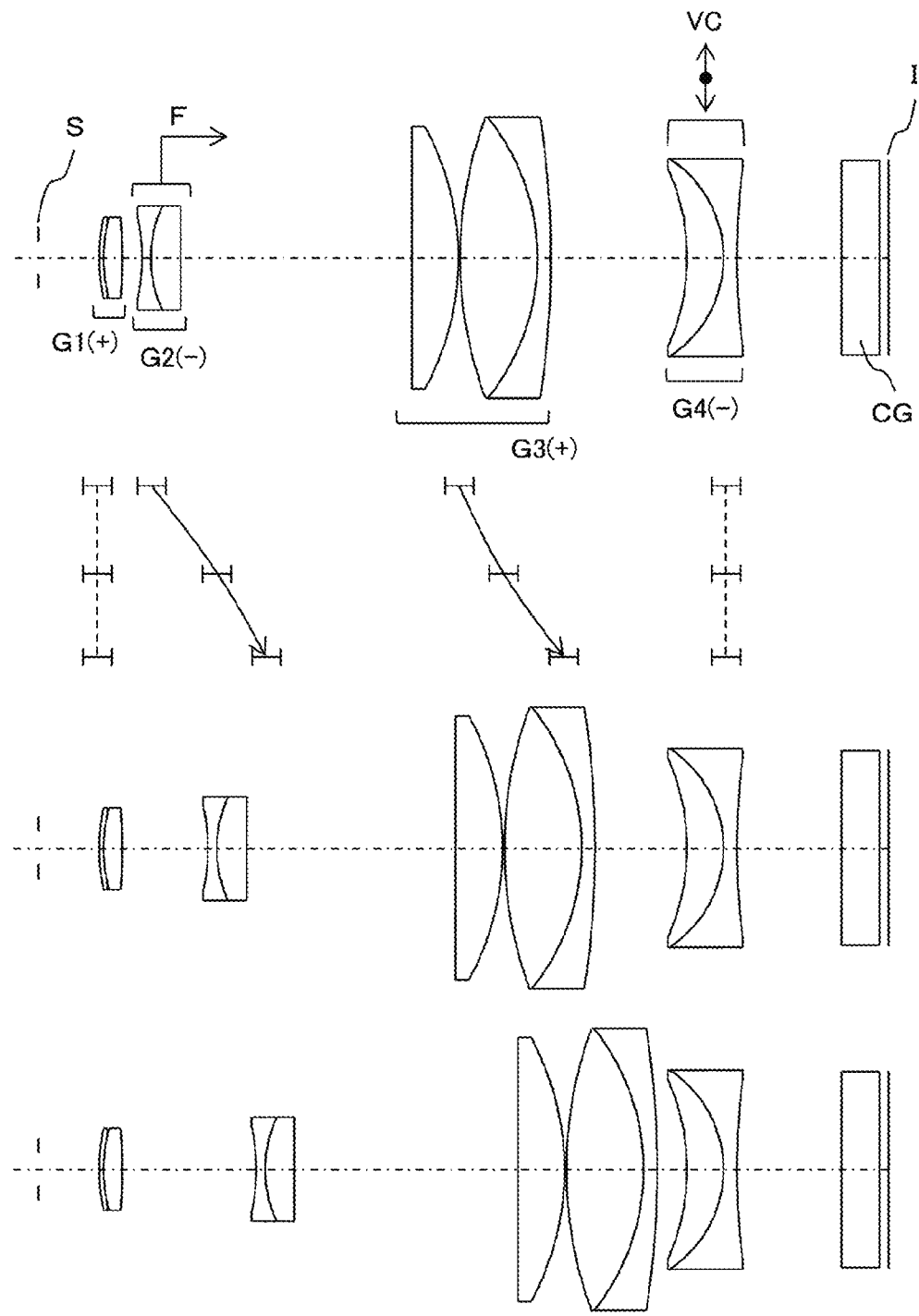
FIG. 11 is a diagram illustrating a lens construction example of a variable magnification optical system in Example 3 of the present invention, where the upper part is a lens construction diagram at a wide angle end, and the lower part is a lens construction diagram at a telephoto end.

FIG. 11 is a cross-sectional view illustrating a lens construction example of a variable magnification optical system in Example 3 according to the present invention. As illustrated in FIG. 11, the variable magnification optical system in Example 3 includes a first lens group G1 having positive refractive power, a second lens group G2 having negative refractive power, a third lens group G3 having positive refractive power, and a fourth lens group G4 having negative refractive power in this order from the object side. The variable magnification optical system is used while being connected to an ocular section in a rigid endoscope not illustrated. Note that, the specific lens construction of each of the lens groups is as illustrated in FIG. 11. Note that, the second lens group G2 is a negative movable lens group for the present invention, the third lens group G3 is a positive movable lens group, and the fourth lens group G4 is a final lens group.

When zooming from a wide angle end to a telephoto end, the first lens group G1 and the fourth lens group G4 are fixed in the optical axis direction, and the second lens group G2 and the third lens group G3 respectively move toward the image side through different trajectories. At the time of focusing on a nearest point object from a farthest point object, the second lens group G2 moves toward the image side. The fourth lens group G4 is constructed to be movable in a direction perpendicular to the optical axis. By moving the fourth lens group G4 in the direction perpendicular to the optical axis, it is possible to correct image blurring such as hand-shake blurring occurred at the time of imaging. An amount of movement of a vibration-compensation group is 0.640 mm when an amount of angle change by moving the vibration-compensation group by a prescribed amount in the direction perpendicular to the optical axis at the time of hand-shake correction is set to 0.3 degrees.

(2) Numerical Value Examples

Next, numerical value examples to which specific numerical values of the variable magnification optical system are applied will be described. Table 11 illustrates surface data of the variable magnification optical system, Table 12 illustrates various types of data, Table 13 illustrates data relating to each of the lens groups composing the variable magnification optical system, Table 14 illustrates a lateral magnification or the like of each of the lens groups, and Table 15 illustrates a maximum imaging magnification or the like at the telephoto end of the variable magnification optical system. Table 26 illustrates the respective numerical values of above-described conditional expressions (1) to (4) in the variable magnification optical system.

Figure 12:
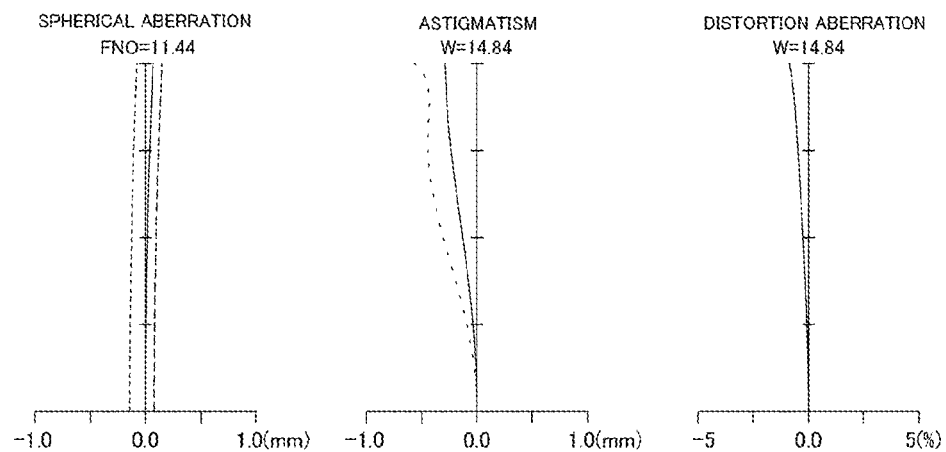
FIG. 12 illustrates spherical aberration, astigmatism, and distortion aberration at the time of focusing on a farthest point object in a wide angle end state of the variable magnification optical system in Example 3 of the present invention.
Figure 13:
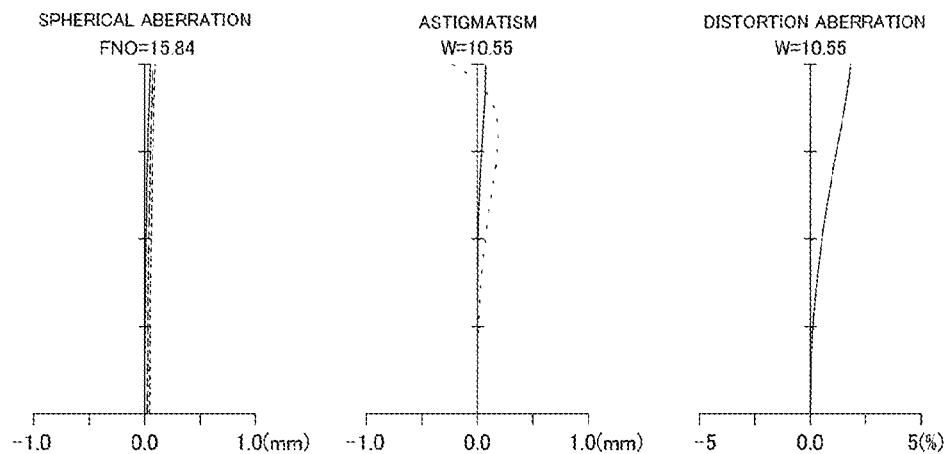
FIG. 13 illustrates spherical aberration, astigmatism, and distortion aberration at the time of focusing on the farthest point object at an intermediate focal position of the variable magnification optical system in Example 3 of the present invention.
Figure 14:
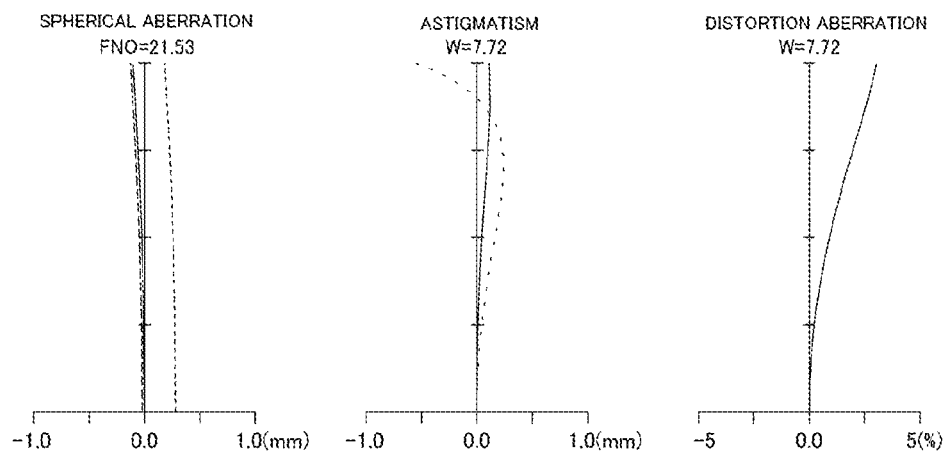
FIG. 14 illustrates spherical aberration, astigmatism, and distortion aberration at the time of focusing on the farthest point object in a telephoto end state of the variable magnification optical system in Example 3 of the present invention.
Figure 15:
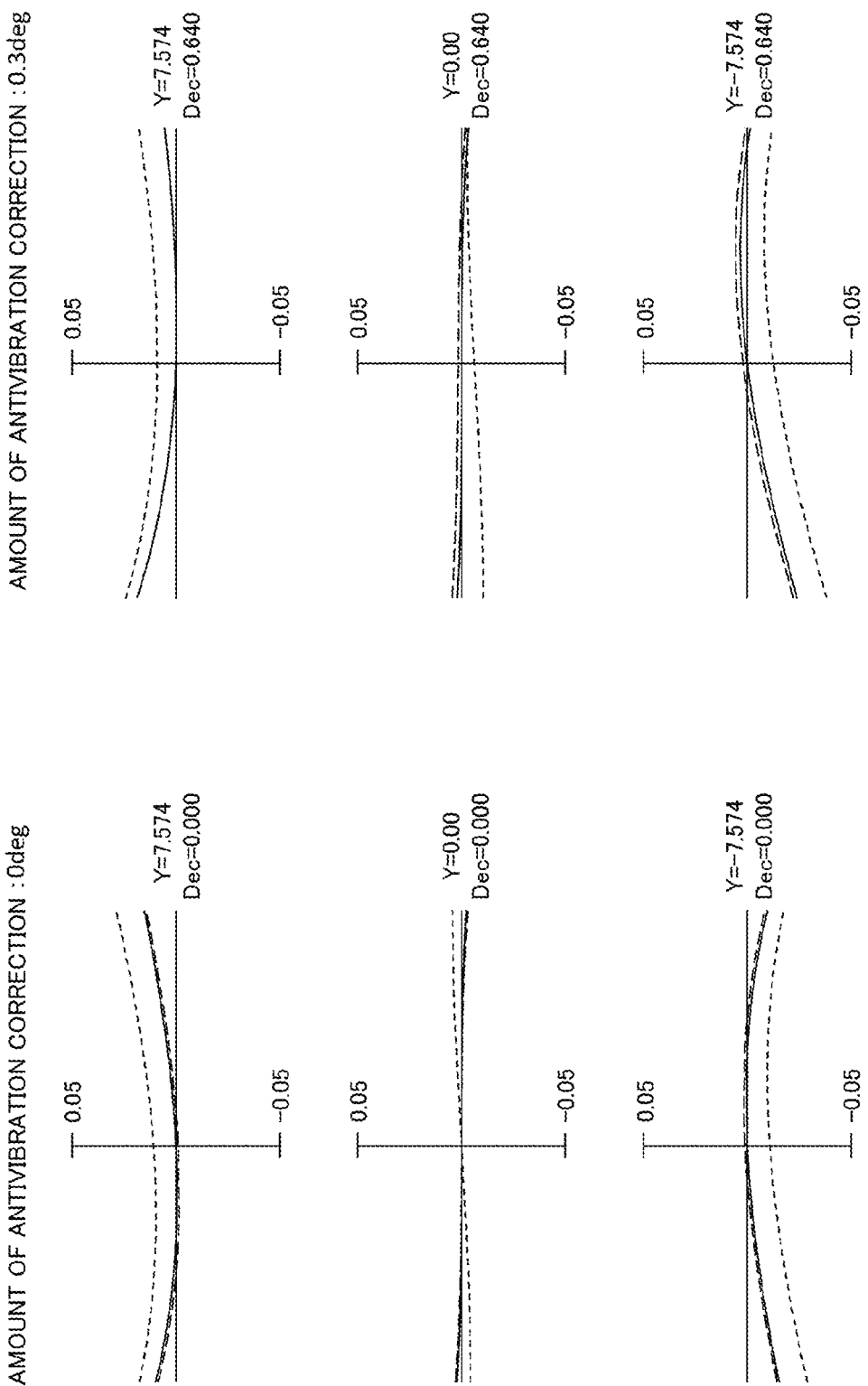
FIG. 15 is a lateral aberration diagram in the telephoto end state of the variable magnification optical system in Example 3 of the present invention.

FIG. 12 to FIG. 14 each illustrate spherical aberration, astigmatism, and distortion aberration at the time of infinity focusing in a wide angle end state, an intermediate focal length state, and a telephoto end state of the variable magnification optical system in Example 3. FIG. 15 illustrates lateral aberration diagrams at the telephoto end of the variable magnification optical system in Example 3.

TABLE 11

| Surface number | r | d | nd | vd | |
|---|---|---|---|---|---|
| 1 | ∞ | 6.852 | | | (Aperture stop) |
| 2 | 21.319 | 0.500 | 1.8467 | 23.78 | |
| 3 | 16.922 | 2.047 | 1.4970 | 81.61 | |
| 4 | −55.920 | d4 | | | |
| 5 | −22.209 | 1.000 | 1.8348 | 42.72 | |
| 6 | 13.561 | 3.284 | 1.7618 | 26.61 | |
| 7 | 2008.731 | d7 | | | |
| 8 | ∞ | 5.203 | 1.6230 | 58.12 | |
| 9 | −30.090 | 0.200 | | | |
| 10 | 44.482 | 8.560 | 1.7433 | 49.22 | |
| 11 | −24.540 | 1.500 | 1.8467 | 23.78 | |
| 12 | −101.496 | d12 | | | |
| 13 | −24.067 | 4.045 | 1.8467 | 23.78 | |
| 14 | −12.980 | 1.500 | 1.7205 | 34.71 | |
| 15 | 78.037 | 11.624 | | | |
| 16 | ∞ | 4.200 | 1.5168 | 64.20 | |
| 17 | ∞ | 1.000 | | | |

TABLE 12

Zoom ratio 1.881, Image height 10.820

| | Wide angle end | Intermediate focal position | Telephoto end |
|---|---|---|---|
| Focal length | 41.197 | 57.040 | 77.501 |
| F number | 11.444 | 15.845 | 21.528 |
| Half image viewing angle | 14.837 | 10.550 | 7.716 |
| Total lens length | 94.336 | 94.336 | 94.336 |
| Back focus | 15.389 | 15.389 | 15.389 |
| d4 | 2.183 | 9.497 | 14.873 |
| d7 | 25.631 | 23.217 | 24.709 |
| d12 | 15.078 | 10.178 | 3.310 |

TABLE 13

| Group | Start surface | Focal length | Lens construction length | Amount of lens movement |
|---|---|---|---|---|
| First lens group | 1 | 35.932 | 9.329 | 0.000 |
| Second lens group | 5 | −22.989 | 4.284 | 12.690 |
| Third lens group | 8 | 24.709 | 15.462 | 11.768 |
| Fourth lens group | 13 | −28.694 | 5.545 | 0.000 |

TABLE 14

| Group | Start surface | Wide angle end | Intermediate focal position | Telephoto end |
|---|---|---|---|---|
| First lens group | 1 | 0.000 | 0.000 | 0.000 |
| Second lens group | 5 | −2.462 | −11.358 | 6.858 |
| Third lens group | 8 | −0.285 | −0.086 | 0.192 |
| Fourth lens group | 13 | 1.636 | 1.634 | 1.634 |

TABLE 15

| Minimum imaging distance | d4 | d7 | Maximum imaging magnification |
|---|---|---|---|
| 90.000 | 36.362 | 3.220 | −1.104 |

Example 4

(1) Construction of Optical System

Figure 16:
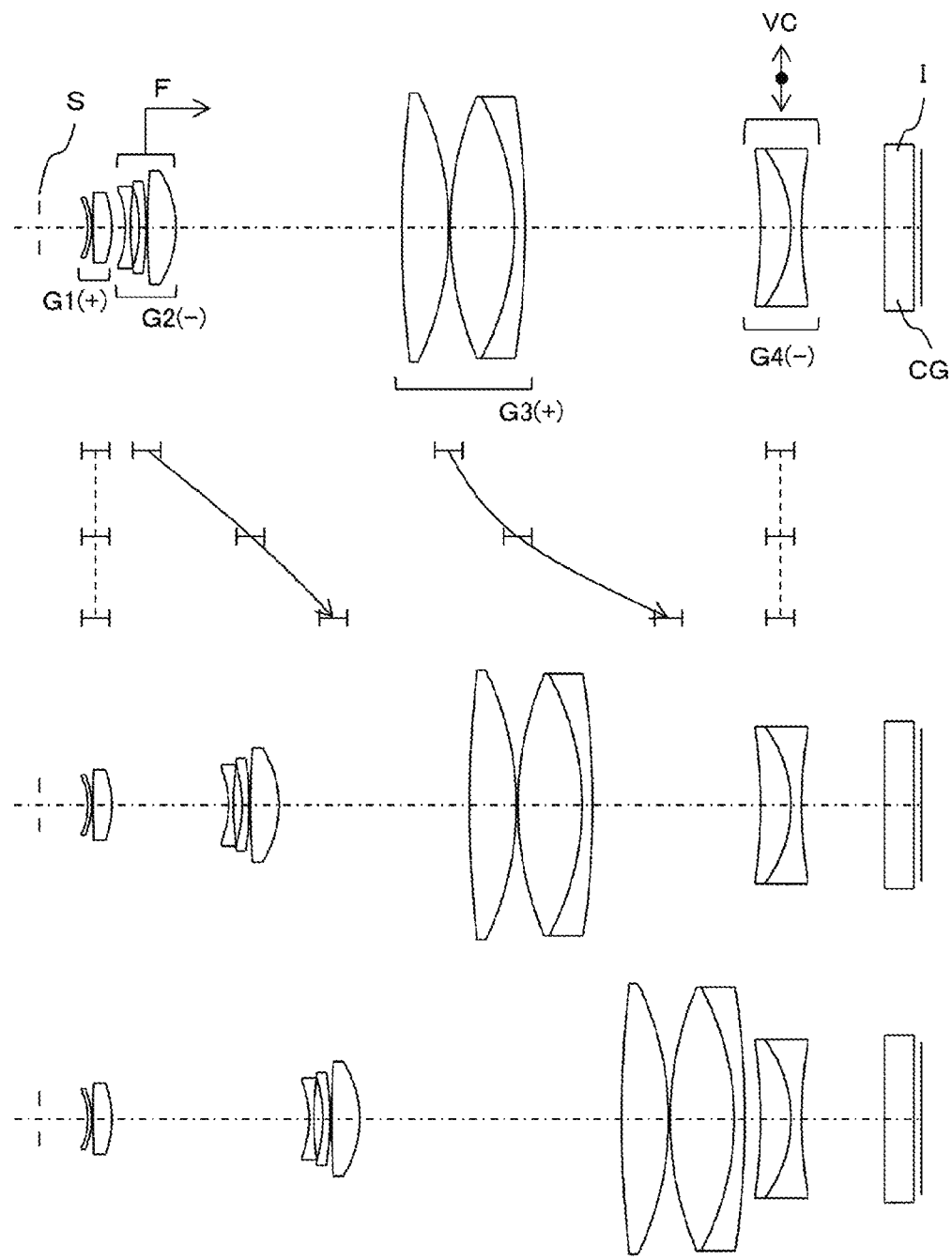
FIG. 16 is a diagram illustrating a lens construction example of a variable magnification optical system in Example 4 of the present invention, where the upper part is a lens construction diagram at a wide angle end, and the lower part is a lens construction diagram at a telephoto end.

FIG. 16 is a cross-sectional view illustrating a lens construction example of a variable magnification optical system in Example 4 according to the present invention. As illustrated in FIG. 16, the variable magnification optical system in Example 4 includes a first lens group G1 having positive refractive power, a second lens group G2 having negative refractive power, a third lens group G3 having positive refractive power, and a fourth lens group G4 having negative refractive power in this order from the object side. The variable magnification optical system is used while being connected to an ocular section in a rigid endoscope not illustrated. Note that, the specific lens construction of each of the lens groups is as illustrated in FIG. 16. Note that, the second lens group G2 is a negative movable lens group for the present invention, the third lens group G3 is a positive movable lens group, and the fourth lens group G4 is a final lens group.

When zooming from a wide angle end to a telephoto end, the first lens group G1 and the fourth lens group G4 are fixed in the optical axis direction, and the second lens group G2 and the third lens group G3 respectively move toward the image side through different trajectories. At the time of focusing on a nearest point object from a farthest point object, the second lens group G2 moves toward the image side. The fourth lens group G4 is constructed to be movable in a direction perpendicular to the optical axis. By moving the fourth lens group G4 in the direction perpendicular to the optical axis, it is possible to correct image blurring such as hand-shake blurring occurred at the time of imaging. An amount of movement of a vibration-compensation group is 1.416 mm when an amount of angle change by moving the vibration-compensation group by a prescribed amount in the direction perpendicular to the optical axis at the time of camera shake correction is set to 0.3 degrees.

(2) Numerical Value Examples Next, numerical value examples to which specific numerical values of the variable magnification optical system are applied will be described. Table 16 illustrates surface data of the variable magnification optical system, Table 17 illustrates various types of data, Table 18 illustrates data relating to each of the lens groups composing the variable magnification optical system, Table 19 illustrates a lateral magnification or the like of each of the lens groups, and Table 20 illustrates a maximum imaging magnification or the like at the telephoto end of the variable magnification optical system. Table 26 illustrates the respective numerical values of above-described conditional expressions (1) to (4) in the variable magnification optical system.

Figure 17:
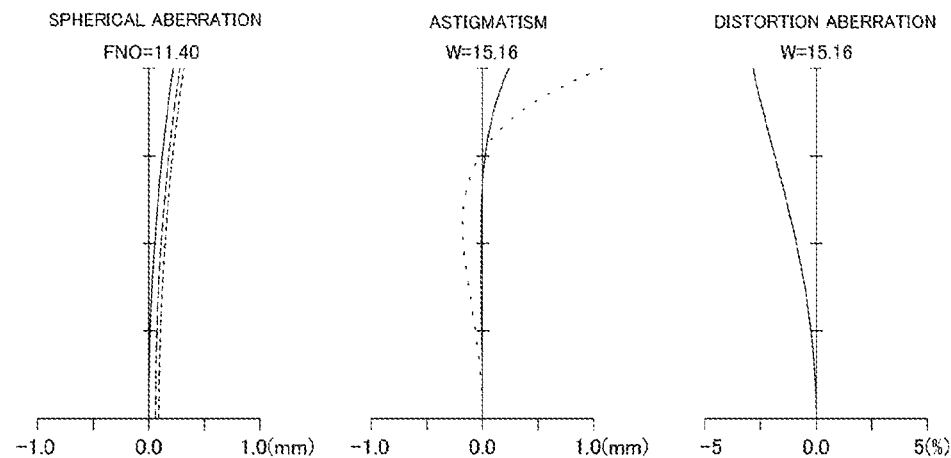
FIG. 17 illustrates spherical aberration, astigmatism, and distortion aberration at the time of focusing on a farthest point object in a wide angle end state of the variable magnification optical system in Example 4 of the present invention.
Figure 18:
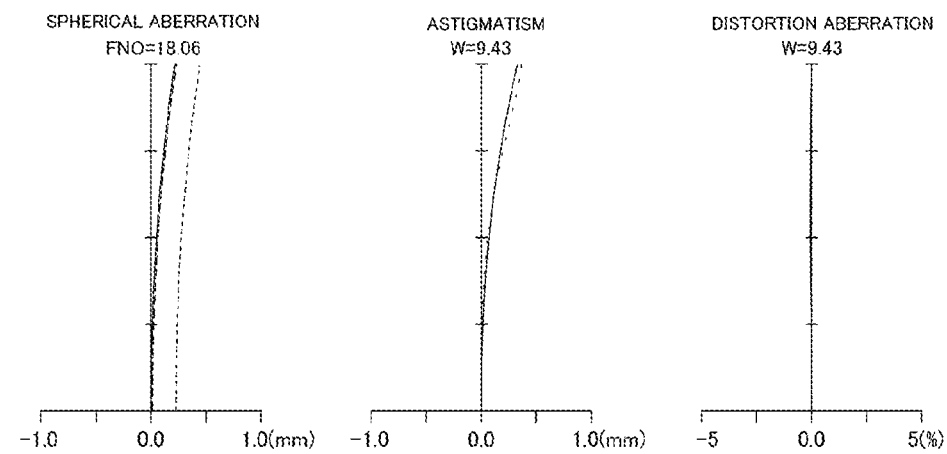
FIG. 18 illustrates spherical aberration, astigmatism, and distortion aberration at the time of focusing on the farthest point object at an intermediate focal position of the variable magnification optical system in Example 4 of the present invention.
Figure 19:
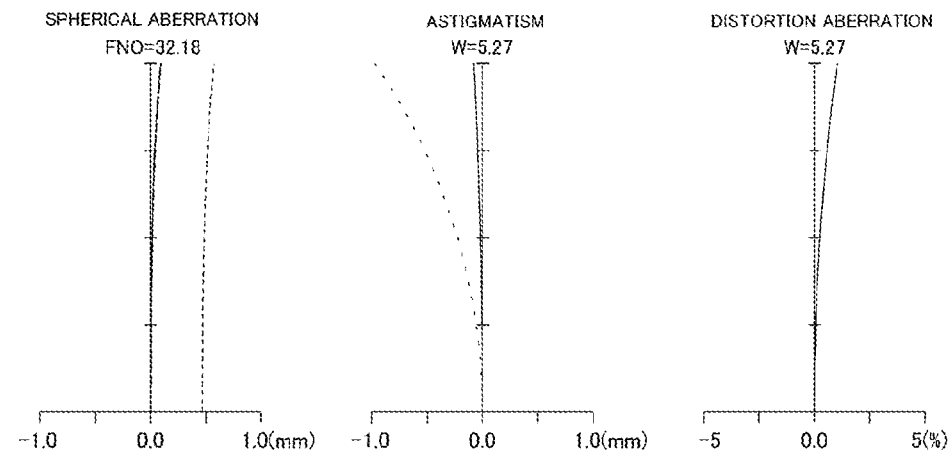
FIG. 19 illustrates spherical aberration, astigmatism, and distortion aberration at the time of focusing on the farthest point object in a telephoto end state of the variable magnification optical system in Example 4 of the present invention.
Figure 20:
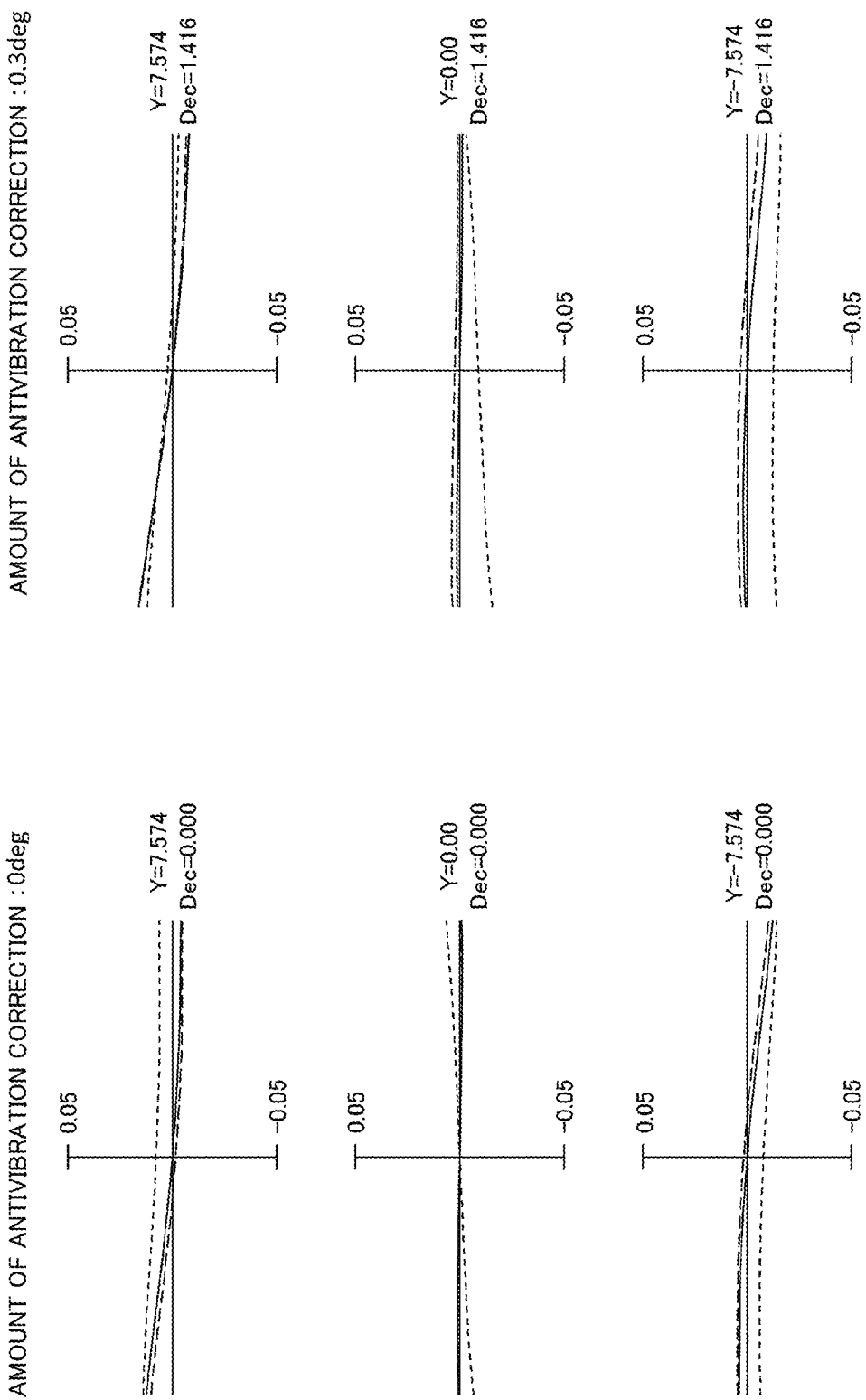
FIG. 20 is a lateral aberration diagram in the telephoto end state of the variable magnification optical system in Example 4 of the present invention.

FIG. 17 to FIG. 19 each illustrate spherical aberration, astigmatism, and distortion aberration at the time of infinity focusing in a wide angle end state, an intermediate focal length state, and a telephoto end state of the variable magnification optical system in Example 4. FIG. 20 illustrates lateral aberration diagrams at the telephoto end of the variable magnification optical system in Example 4.

TABLE 16

| Surface number | r | d | nd | vd | |
|---|---|---|---|---|---|
| 1 | ∞ | 6.852 | | | (Aperture stop) |
| 2 | −9.018 | 0.500 | 1.8503 | 32.27 | |
| 3 | −10.789 | 0.200 | | | |
| 4 | 308.653 | 2.660 | 1.4970 | 81.61 | |
| 5 | −14.998 | d5 | | | |
| 6 | −14.091 | 0.700 | 1.8348 | 42.72 | |
| 7 | 44.283 | 1.240 | | | |
| 8 | −19.461 | 1.000 | 1.8348 | 42.72 | |
| 9 | −42.747 | 0.200 | | | |
| 10 | 120.455 | 4.022 | 1.6477 | 33.84 | |
| 11 | −15.011 | d11 | | | |
| 12 | 164.593 | 6.656 | 1.6385 | 55.45 | |
| 13 | −43.550 | 0.200 | | | |
| 14 | 47.160 | 9.112 | 1.4970 | 81.61 | |
| 15 | −38.350 | 1.500 | 1.8467 | 23.78 | |
| 16 | −124.286 | d16 | | | |
| 17 | −74.575 | 4.318 | 1.8467 | 23.78 | |
| 18 | −18.298 | 1.500 | 1.8503 | 32.27 | |
| 19 | 63.815 | 11.766 | | | |
| 20 | ∞ | 4.200 | 1.5168 | 64.20 | |
| 21 | ∞ | 1.000 | | | |

TABLE 17

Zoom ratio 2.822, Image height 10.820

| | Wide angle end | Intermediate focal position | Telephoto end |
|---|---|---|---|
| Focal length | 41.042 | 65.022 | 115.840 |
| F number | 11.401 | 18.062 | 32.178 |
| Half image viewing angle | 15.164 | 9.434 | 5.274 |
| Total lens length | 125.000 | 125.000 | 125.000 |
| Back focus | 15.531 | 15.531 | 15.531 |
| d5 | 1.960 | 16.551 | 27.994 |
| d11 | 32.024 | 27.029 | 37.155 |
| d16 | 33.390 | 23.795 | 2.226 |

TABLE 18

| Group | Start length | Focal surface | Lens construction length | Amount of lens movement |
|---|---|---|---|---|
| First lens group | 1 | 43.553 | 10.212 | 0.000 |
| Second lens group | 6 | −29.026 | 7.162 | 26.034 |
| Third lens group | 12 | 37.498 | 17.468 | 31.164 |
| Fourth lens group | 17 | −39.436 | 5.818 | 0.000 |

TABLE 19

| Group | Start surface | Wide angle end | Intermediate focal position | Telephoto end |
|---|---|---|---|---|
| First lens group | 1 | 0.000 | 0.000 | 0.000 |
| Second lens group | 6 | −1.433 | −5.120 | 5.028 |
| Third lens group | 12 | −0.461 | −0.204 | 0.371 |
| Fourth lens group | 17 | 1.427 | 1.426 | 1.425 |

TABLE 20

| Minimum imaging distance | d5 | d11 | Maximum imaging magnification |
|---|---|---|---|
| 120.000 | 50.530 | 14.619 | −1.134 |

Example 5

(1) Construction of Optical System

Figure 21:
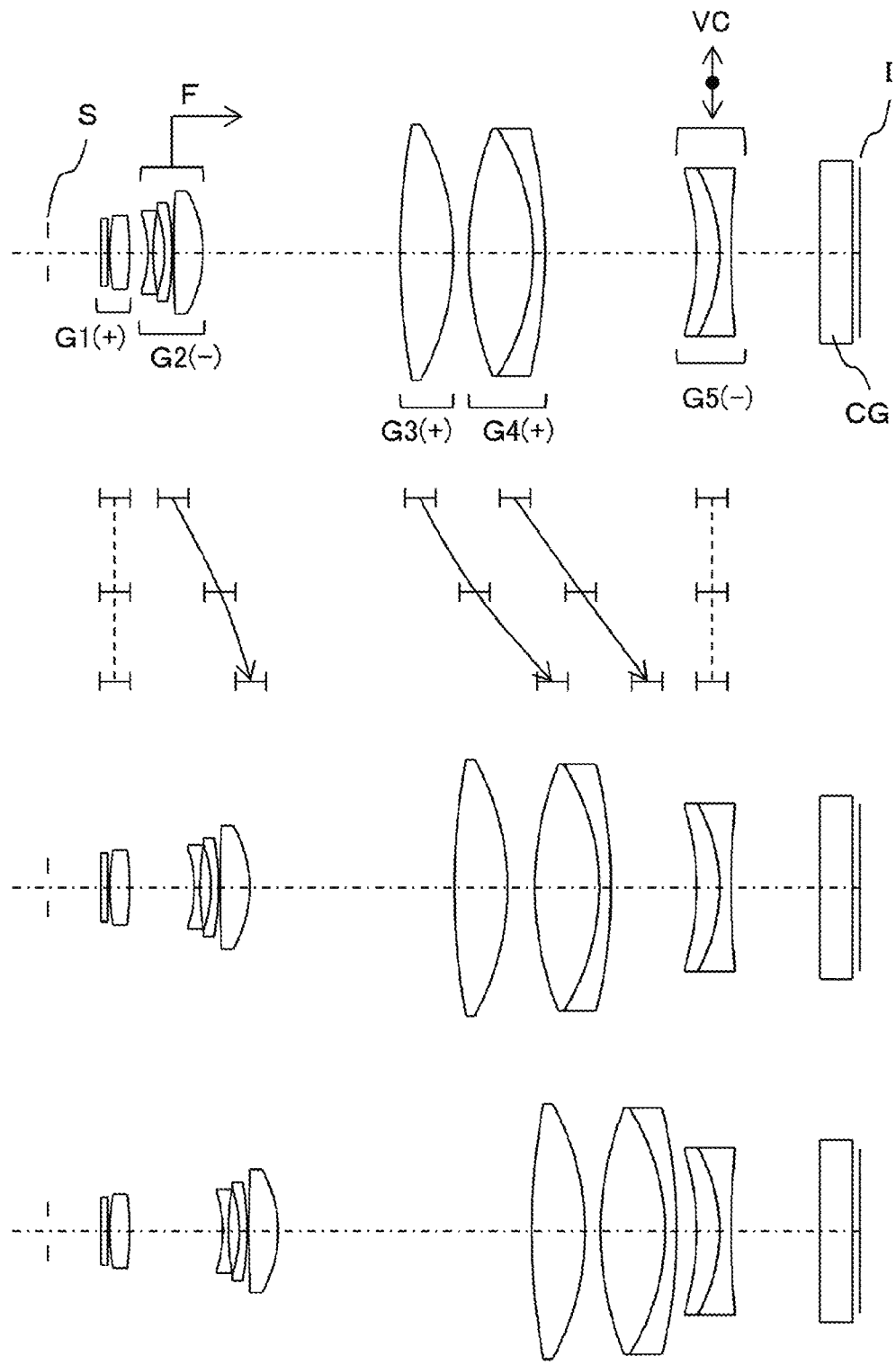
FIG. 21 is a diagram illustrating a lens construction example of a variable magnification optical system in Example 5 of the present invention, where the upper part is a lens construction diagram at a wide angle end, and the lower part is a lens construction diagram at a telephoto end.

FIG. 21 is a cross-sectional view illustrating a lens construction example of a variable magnification optical system in Example 5 according to the present invention. As illustrated in FIG. 21, the variable magnification optical system in Example 5 includes a first lens group G1 having positive refractive power, a second lens group G2 having negative refractive power, a third lens group G3 having positive refractive power, a fourth lens group G4 having a positive refractive power, and a fifth lens group G4 having negative refractive power in this order from the object side. The variable magnification optical system is used while being connected to an ocular section in a rigid endoscope not illustrated. Note that, the specific lens construction of each of the lens groups is as illustrated in FIG. 16. Note that, the second lens group G2 is a negative movable lens group for the present invention, the third lens group G3 is a positive movable lens group, and the fifth lens group G5 is a final lens group.

When zooming from a wide angle end to a telephoto end, the first lens group G1 and the fourth lens group G4 are fixed in the optical axis direction, and the second lens group G2, the third lens group G3, and the fourth lens group G4 respectively move toward the image side through different trajectories. At the time of focusing on a nearest point object from a farthest point object, the second lens group G2 moves toward the image side. The fifth lens group G5 is constructed to be movable in a direction perpendicular to the optical axis. By moving the fifth lens group G5 in the direction perpendicular to the optical axis, it is possible to correct image blurring such as hand-shake blurring occurred at the time of imaging. An amount of movement of a vibration-compensation group is 0.823 mm when an amount of angle change by moving the vibration-compensation group by a prescribed amount in the direction perpendicular to the optical axis at the time of camera shake correction is set to 0.3 degrees.

(2) Numerical Value Examples

Next, numerical value examples to which specific numerical values of the variable magnification optical system are applied will be described. Table 21 illustrates surface data of the variable magnification optical system, Table 22 illustrates various types of data, Table 23 illustrates data relating to each of the lens groups composing the variable magnification optical system, Table 24 illustrates a lateral magnification or the like of each of the lens groups, and Table 25 illustrates a maximum imaging magnification or the like at the telephoto end of the variable magnification optical system. Table 26 illustrates the respective numerical values of above-described conditional expressions (1) to (4) in the variable magnification optical system.

Figure 22:
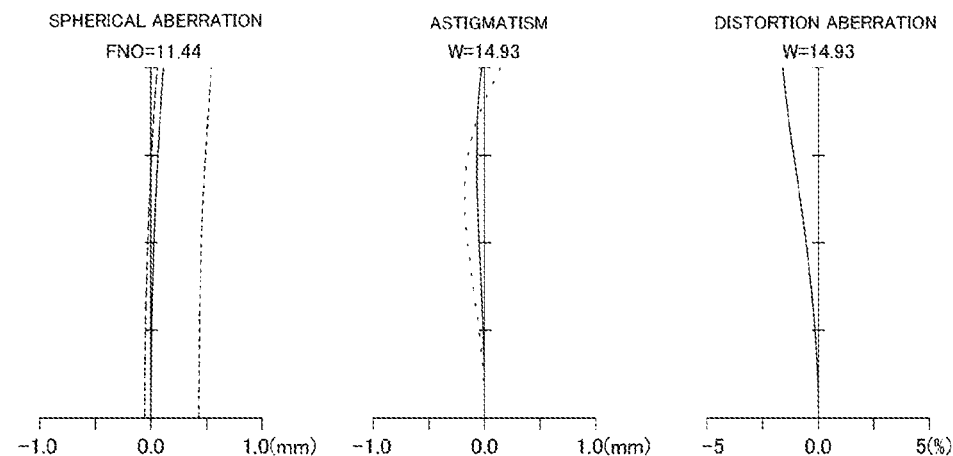
FIG. 22 illustrates spherical aberration, astigmatism, and distortion aberration at the time of focusing on the farthest point object in a wide angle end state of the variable magnification optical system in Example 5 of the present invention.
Figure 23:
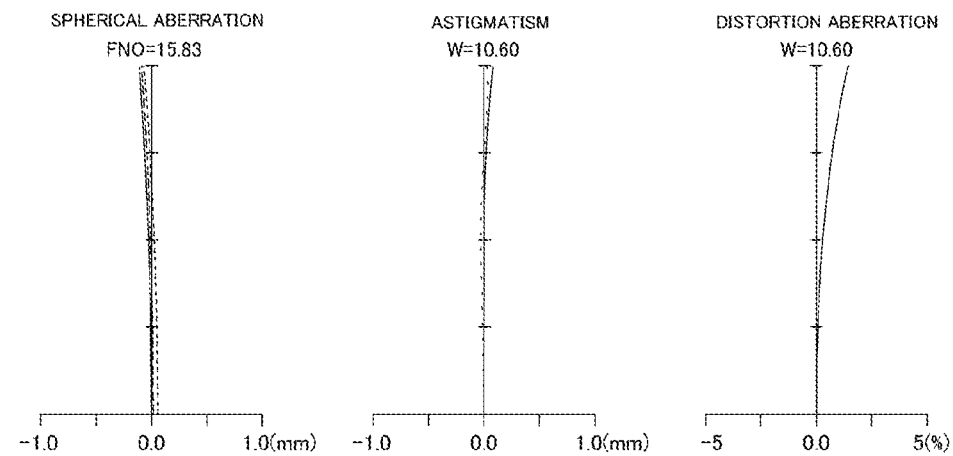
FIG. 23 illustrates spherical aberration, astigmatism, and distortion aberration at the time of focusing on the farthest point object at an intermediate focal position of the variable magnification optical system in Example 5 of the present invention.
Figure 24:
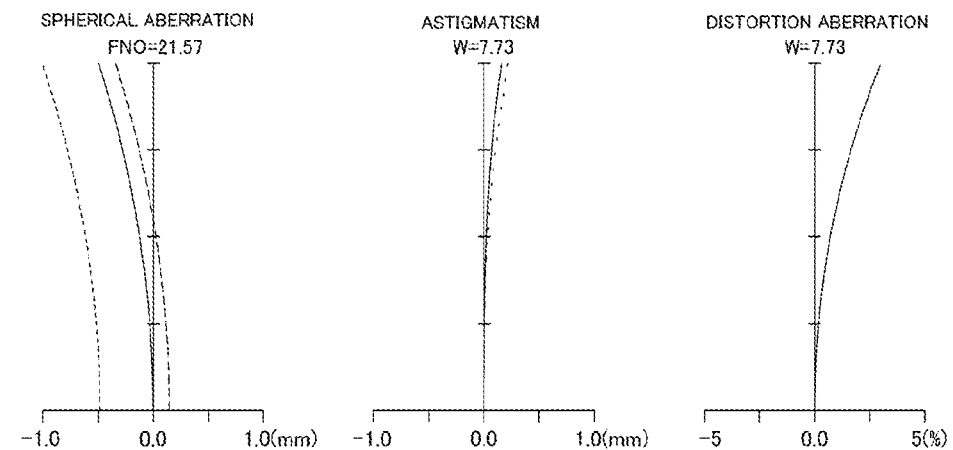
FIG. 24 illustrates spherical aberration, astigmatism, and distortion aberration at the time of focusing on the farthest point object in a telephoto end state of the variable magnification optical system in Example 5 of the present invention.

FIG. 21 to FIG. 23 each illustrate spherical aberration, astigmatism, and distortion aberration at the time of infinity focusing in a wide angle end state, an intermediate focal length state, and a telephoto end state of the variable magnification optical system in Example 5. FIG. 25 illustrates lateral aberration diagrams at the telephoto end of the variable magnification optical system in Example 5.

TABLE 21

| Surface number | r | d | nd | vd | |
|---|---|---|---|---|---|
| 1 | ∞ | 6.852 | | | (Aperture stop) |
| 2 | ∞ | 0.900 | 1.5233 | 54.52 | |
| 3 | ∞ | 0.200 | | | |
| 4 | 23.512 | 2.583 | 1.4970 | 81.61 | |
| 5 | −34.064 | d5 | | | |
| 6 | −15.303 | 0.700 | 2.0006 | 25.46 | |
| 7 | 29.326 | 1.425 | | | |
| 8 | −16.734 | 1.000 | 1.8340 | 37.35 | |
| 9 | −35.909 | 0.200 | | | |
| 10 | 154.756 | 3.817 | 1.8467 | 23.78 | |
| 11 | −15.831 | d11 | | | |
| 12 | 90.450 | 6.880 | 1.4970 | 81.61 | |
| 13 | −33.891 | d13 | | | |
| 14 | 42.986 | 8.332 | 1.4970 | 81.61 | |
| 15 | −29.467 | 1.500 | 1.8467 | 23.78 | |
| 16 | −67.407 | d16 | | | |
| 17 | −34.956 | 2.959 | 1.8467 | 23.78 | |
| 18 | −21.633 | 1.500 | 1.7725 | 49.62 | |
| 19 | 104.617 | 11.460 | | | |
| 20 | ∞ | 4.200 | 1.5168 | 64.20 | |
| 21 | ∞ | 1.000 | | | |

TABLE 22

Zoom ratio 1.885, Image height 10.820

| | Wide angle end | Intermediate focal position | Telephoto end |
|---|---|---|---|
| Focal length | 41.202 | 57.002 | 77.661 |
| F number | 11.445 | 15.834 | 21.572 |
| Half image viewing angle | 14.928 | 10.604 | 7.726 |
| Total lens length | 104.977 | 104.977 | 104.977 |
| Back focus | 15.226 | 15.226 | 15.226 |
| d5 | 2.385 | 8.392 | 12.090 |
| d11 | 25.479 | 26.474 | 32.798 |
| d13 | 2.000 | 3.531 | 2.000 |
| d16 | 19.606 | 11.073 | 2.582 |

TABLE 23

| Group | Start surface | Focal length | Lens construction length | Amount of lens movement |
|---|---|---|---|---|
| First lens group | 1 | 28.412 | 10.535 | 0.000 |
| Second lens group | 6 | −24.720 | 7.141 | 9.705 |
| Third lens group | 12 | 50.534 | 6.880 | 17.024 |
| Fourth lens group | 14 | 81.921 | 9.832 | 17.024 |
| Fifth lens group | 17 | −35.138 | 4.459 | 0.000 |

TABLE 24

| Group | Start surface | Wide angle end | Intermediate focal position | Telephoto end |
|---|---|---|---|---|
| First lens group | 1 | 0.000 | 0.000 | 0.000 |
| Second lens group | 6 | −4.298 | 96.509 | 6.252 |
| Third lens group | 12 | −0.413 | 0.021 | 0.386 |
| Fourth lens group | 14 | 0.550 | 0.653 | 0.755 |
| Fifth lens group | 17 | 1.485 | 1.491 | 1.501 |

TABLE 25

| Minimum imaging distance | d5 | d11 | Maximum imaging magnification |
|---|---|---|---|
| 90.000 | 23.794 | 21.094 | −1.035 |

TABLE 26

| | Example 1 | Example 2 | Example 3 | Example 4 | Example 5 |
|---|---|---|---|---|---|
| Conditional expression (1) | −1.03 | −1.08 | −1.10 | −1.13 | −1.04 |
| Conditional expression (2) | 1.50 | 1.52 | 1.63 | 1.43 | 1.50 |
| Conditional expression (3) | 0.57 | 0.93 | 1.08 | 0.84 | 0.57 |

TABLE 26-continued

|  | Example 1 | Example 2 | Example 3 | Example 4 | Example 5 |
|---|---|---|---|---|---|
| Conditional expression (4) | 0.63 | 0.60 | 0.51 | 0.57 | 0.62 |
| bt | −1.03 | −1.08 | −1.10 | −1.13 | −1.04 |
| bit | 1.50 | 1.52 | 1.63 | 1.43 | 1.50 |
| mn | 9.81 | 13.31 | 12.69 | 26.03 | 9.71 |
| mp | 17.07 | 14.36 | 11.77 | 31.16 | 17.02 |
| fi | −35.83 | −34.08 | −28.69 | −39.44 | −35.14 |
| fw | 41.20 | 41.16 | 41.20 | 41.04 | 41.20 |
| ft | 77.64 | 77.55 | 77.50 | 115.84 | 77.66 |

(Example of Imaging Apparatus)

Next, an example of an imaging apparatus according to the present invention will be described. The imaging apparatus 10 according to the present invention is used while being connected to a rigid endoscope 20 (the observation optical system). The imaging apparatus 10 includes a lens unit that houses a variable magnification optical system 11 according to the present invention and an imaging apparatus main body 12 on which the lens unit is interchangeably mounted. The lens unit can house any one of the above-described variable magnification optical systems in Examples 1 to 5, for example. Flat plates (surface numbers 1 and 2) arranged closest to the object side in the first lens group G1 in the respective examples are cover glasses, which prevent dust, water, or the like from entering a lens unit housing (lens barrel) from the object side (ocular section side). A lens arranged closest to the image side in the variable magnification optical system 11 and the lens unit housing are sealed, and dust, water, or the like is prevented from entering the lens unit housing from the image side. Since the lens unit is thus made to have a sealed structure, it is possible to easily perform disinfection, bacteria elimination, sterilization, and the like. An image sensor 13 (I) is arranged within the imaging apparatus main body 12, and a cover glass (CG) is arranged on the object side of the image sensor 13. A display device 14 such as a liquid crystal monitor is provided on a back surface side of the imaging apparatus main body.

The rigid endoscope 20 includes a lens barrel section 21 that houses an objective lens system (not illustrated), a relay lens system (not illustrated), and an ocular lens system (not illustrated), a light source 22, and an illumination optical system 23 in this order from the object side. The lens barrel section 21 is formed in a long shape along a total optical length, and its object side corresponds to the above-described insertion section, and is inserted into the body of a patient, for example. An image side of the lens barrel section 21 corresponds to the above-described ocular section. A doctor, for example, can observe the inside of the body, i.e., an affected site or the like of the patient via the ocular section. A lens unit is connected to the ocular section. The light source 22 is provided outside the lens barrel section 21 and in the vicinity of the ocular section. The illumination optical system 23 transmits illumination light from the light source 22 to the object side of the lens barrel section 21, to illuminate the affected site or the like. Although not shown in FIG. 26, the imaging apparatus main body 11 and a personal computer or the like including the above-described image processing section may be connected to each other via a communication connection means, to display a rigid endoscope image (observation image) of the affected site or the like acquired by the rigid endoscope 20 and the imaging apparatus 10 on a display device in the personal computer or the like. The imaging apparatus main body or the personal computer or the like connected to the imaging apparatus main body may be connected to a personal computer or the like at a remote location via a communication connection means such as the Internet to display a rigid endoscope image of the affected site or the like on a display device at the remote location. Such constructions can realize the above-described rigid endoscope image display system (observation image display system).

Note that, in the example of the imaging apparatus, the imaging apparatus 10 and the rigid endoscope 20 are detachably connected to each other. In the example of the imaging apparatus, the lens unit that houses the variable magnification optical system 11 is interchangeably mounted on the imaging apparatus main body 12. However, it goes without saying that the imaging apparatus according to the present invention is not limited to these aspects. The lens unit and the imaging apparatus main body 12 may be integrally (inseparably) constructed, or the imaging apparatus 10 and the rigid endoscope 20 may be integrally constructed.

According to the present invention, it is possible to provide a variable magnification optical system, capable of realizing a high-resolution observation image display system that can arbitrarily change an observation field of view without changing a working distance of an observation optical system while keeping the observation optical system small in size, and an imaging apparatus including the variable magnification optical system.

The invention claimed is:

1. A variable magnification optical system connected to an observation optical system, the variable magnification optical system comprising:
a first lens group arranged closest to an observation optical system side, a final lens group arranged closest to an image side, and a plurality of movable lens groups arranged between the first lens group and the final lens group and movable in an optical axis direction, wherein
the first lens group and the final lens group are fixed in the optical axis direction, and the plurality of movable lens groups are moved in the optical axis direction, to perform zooming, and
at least one of the plurality of movable lens groups is moved in the optical axis direction to perform focusing on a nearest point object from a farthest point object, wherein a following condition is satisfied:

$$1.10 \leq bit \leq 3.00 \tag{2}$$

where
bit: a lateral magnification of the final lens group at a time of focusing on the farthest point object at a telephoto end,
wherein a following condition is satisfied:

$$0.20 \leq |fi|/\sqrt{(fw \times ft)} \leq 1.20 \tag{4}$$

where
fi: a focal length of the final lens group,
fw: a focal length of the variable magnification optical system at a time of focusing on the farthest point object at the wide angle end, and
ft: a focal length of the variable magnification optical system at a time of focusing on the farthest point object at the telephoto end.

2. The variable magnification optical system according to claim 1, wherein a following condition is satisfied:

$$bt \leq -0.80 \tag{1}$$

where
- bt: a maximum imaging magnification at a telephoto end of the variable magnification optical system.

3. The variable magnification optical system according to claim 2, wherein the plurality of movable lens groups include a negative movable lens group having negative refractive power and a positive movable lens group having positive refractive power in order from the observation optical system side.

4. The variable magnification optical system according to claim 2, wherein the final lens group is moved in a direction perpendicular to an optical axis to correct image blurring.

5. The variable magnification optical system according to claim 1, wherein the plurality of movable lens groups include a negative movable lens group having negative refractive power and a positive movable lens group having positive refractive power in order from the observation optical system side.

6. The variable magnification optical system according to claim 5, wherein the negative movable lens group is moved in the optical axis direction to perform the focusing.

7. The variable magnification optical system according to claim 6, wherein a following condition is satisfied:

$$0.40 \le mn/mp \le 2.00 \quad (3)$$

where
- mn: an amount of movement in the optical axis direction of the negative movable lens group at a time of zooming from a wide angle end to a telephoto end, and a sign is positive for movement toward an image side, and
- mp: an amount of movement in the optical axis direction of the positive movable lens group at the time of zooming from the wide angle end to the telephoto end, and a sign is positive for movement toward the image side.

8. The variable magnification optical system according to claim 5, wherein a following condition is satisfied:

$$0.40 \le mn/mp \le 2.00 \quad (3)$$

where
- mn: an amount of movement in the optical axis direction of the negative movable lens group at a time of zooming from a wide angle end to a telephoto end, and a sign is positive for movement toward an image side, and
- mp: an amount of movement in the optical axis direction of the positive movable lens group at the time of zooming from the wide angle end to the telephoto end, and a sign is positive for movement toward the image side.

9. The variable magnification optical system according to claim 1, wherein the final lens group is moved in a direction perpendicular to an optical axis to correct image blurring.

10. An imaging apparatus comprising the variable magnification optical system according to claim 1, and an image sensor that converts into an electrical signal an optical image formed by the variable magnification optical system on an image side of the variable magnification optical system.

11. The variable magnification optical system according to claim 1, wherein the plurality of movable lens groups include a negative movable lens group having negative refractive power and a positive movable lens group having positive refractive power in order from the observation optical system side.

12. The variable magnification optical system according to claim 1, wherein the final lens group is moved in a direction perpendicular to an optical axis to correct image blurring.

* * * * *